United States Patent
Pic et al.

(10) Patent No.: US 11,896,229 B2
(45) Date of Patent: Feb. 13, 2024

(54) GRAPPLING SYSTEMS AND METHODS FOR LUMEN APPOSITION OR WOUND DEFECTS

(71) Applicant: Boston Scientific Scimed, Inc., Maple Grove, MN (US)

(72) Inventors: Andrew Pic, Northboro, MA (US); Joseph W. King, Franklin, MA (US); Gonzalo Jose Saenz Villalobos, Alajuela (CR); Deborah Amaya Pineda, Santa Barbara (CR)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 136 days.

(21) Appl. No.: 17/404,483

(22) Filed: Aug. 17, 2021

(65) Prior Publication Data

US 2022/0061847 A1 Mar. 3, 2022

Related U.S. Application Data

(60) Provisional application No. 63/073,192, filed on Sep. 1, 2020.

(51) Int. Cl.
*A61B 17/11* (2006.01)
*A61B 17/00* (2006.01)

(52) U.S. Cl.
CPC . *A61B 17/1114* (2013.01); *A61B 2017/00477* (2013.01); *A61B 2017/00862* (2013.01); *A61B 2017/1103* (2013.01)

(58) Field of Classification Search
CPC ............ A61B 17/1114; A61B 17/0401; A61B 17/0643; A61B 17/068; A61B 17/0218;
(Continued)

(56) References Cited

U.S. PATENT DOCUMENTS

| 3,958,576 A | 5/1976 | Komiya |
| 5,569,274 A | 10/1996 | Rapacki et al. |

(Continued)

FOREIGN PATENT DOCUMENTS

| WO | 2014022464 A1 | 2/2014 | |
| WO | WO-2014022464 A1 * | 2/2014 | ....... A61B 17/00234 |

(Continued)

OTHER PUBLICATIONS

International Search Report and Written Opinion for the International Patent Application No. PCT/US2021/046285, dated Nov. 17, 2021, 17 pages.

*Primary Examiner* — Vi X Nguyen
(74) *Attorney, Agent, or Firm* — Seager, Tufte & Wickhem, LLP

(57) ABSTRACT

A tissue-manipulating system including a tissue-manipulating device having shaft and a tissue grasper assembly. The tissue grasper assembly has at least one grasper arm resiliently expandable from a closed configuration, within and extending along the longitudinal axis of a shaft, to an open configuration outside the shaft with the grasper arm expanded in a direction transverse to the longitudinal axis of the shaft. In the open configuration, the at least one grasper arm may be engaged with tissue wall to manipulate or move the tissue wall, such as to move a distal tissue wall closer to a proximal tissue wall. The tissue grasper assembly may be deployable (such as by being separated from the shaft), such as to remain in place holding two tissue walls in apposition.

20 Claims, 16 Drawing Sheets

(58) Field of Classification Search
CPC .......... A61B 2017/00477; A61B 2017/00862;
A61B 2017/1103; A61B 2017/0417;
A61B 2017/0419; A61B 2017/0641;
A61B 2017/00349; A61B 2017/00818;
A61B 2090/037

See application file for complete search history.

(56) References Cited

U.S. PATENT DOCUMENTS

| | | |
|---|---|---|
| 6,113,611 A | 9/2000 | Allen et al. |
| 6,485,496 B1 | 11/2002 | Suyker et al. |
| 6,485,596 B1 | 11/2002 | Toyoda et al. |
| 6,616,675 B1 | 9/2003 | Evard et al. |
| 7,717,928 B2 | 5/2010 | Copa et al. |
| 9,888,926 B2 | 2/2018 | Phan et al. |
| 2004/0044364 A1 | 3/2004 | DeVries et al. |
| 2004/0073237 A1 | 4/2004 | Leinsing |
| 2004/0176784 A1 | 9/2004 | Okada |
| 2005/0107871 A1 | 5/2005 | Realyvasquez et al. |
| 2005/0216036 A1 | 9/2005 | Nakao |
| 2005/0251168 A1 | 11/2005 | Hess et al. |
| 2006/0259074 A1 | 11/2006 | Kelleher et al. |
| 2008/0009888 A1 | 1/2008 | Ewers et al. |
| 2008/0243151 A1 | 10/2008 | Binmoeller et al. |
| 2009/0024149 A1 | 1/2009 | Saeed et al. |
| 2010/0268029 A1 | 10/2010 | Phan et al. |
| 2013/0123807 A1* | 5/2013 | Wells .................. A61B 17/083 606/142 |
| 2016/0000433 A1 | 1/2016 | Raybin et al. |
| 2017/0086824 A1 | 3/2017 | Khan |

FOREIGN PATENT DOCUMENTS

| | | |
|---|---|---|
| WO | 2019135236 A1 | 7/2019 |
| WO | 2019140097 A1 | 7/2019 |

* cited by examiner

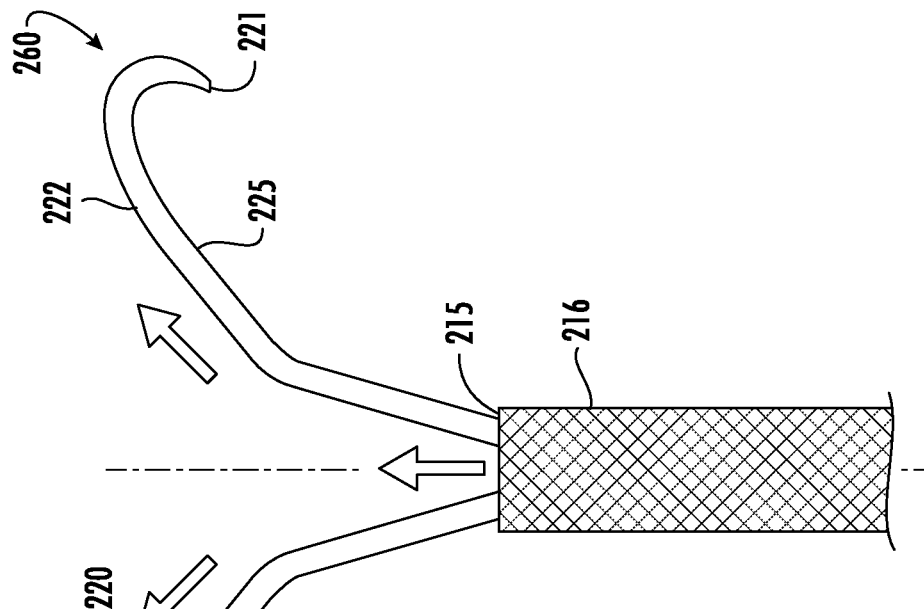
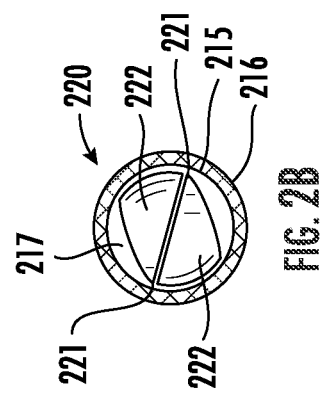
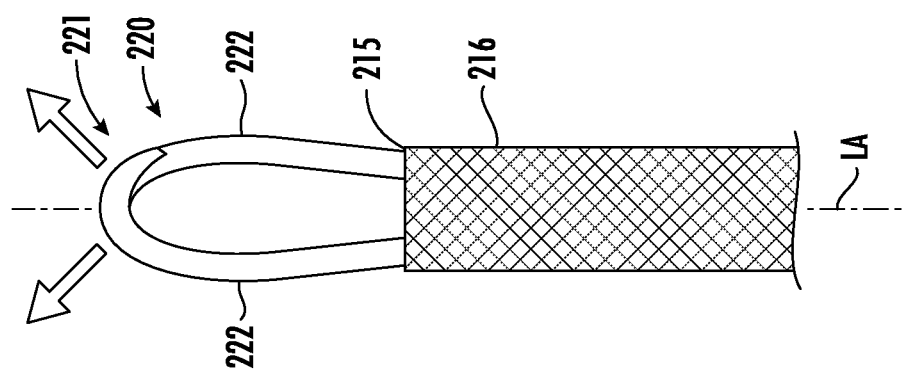
FIG. 2C
FIG. 2B
FIG. 2A

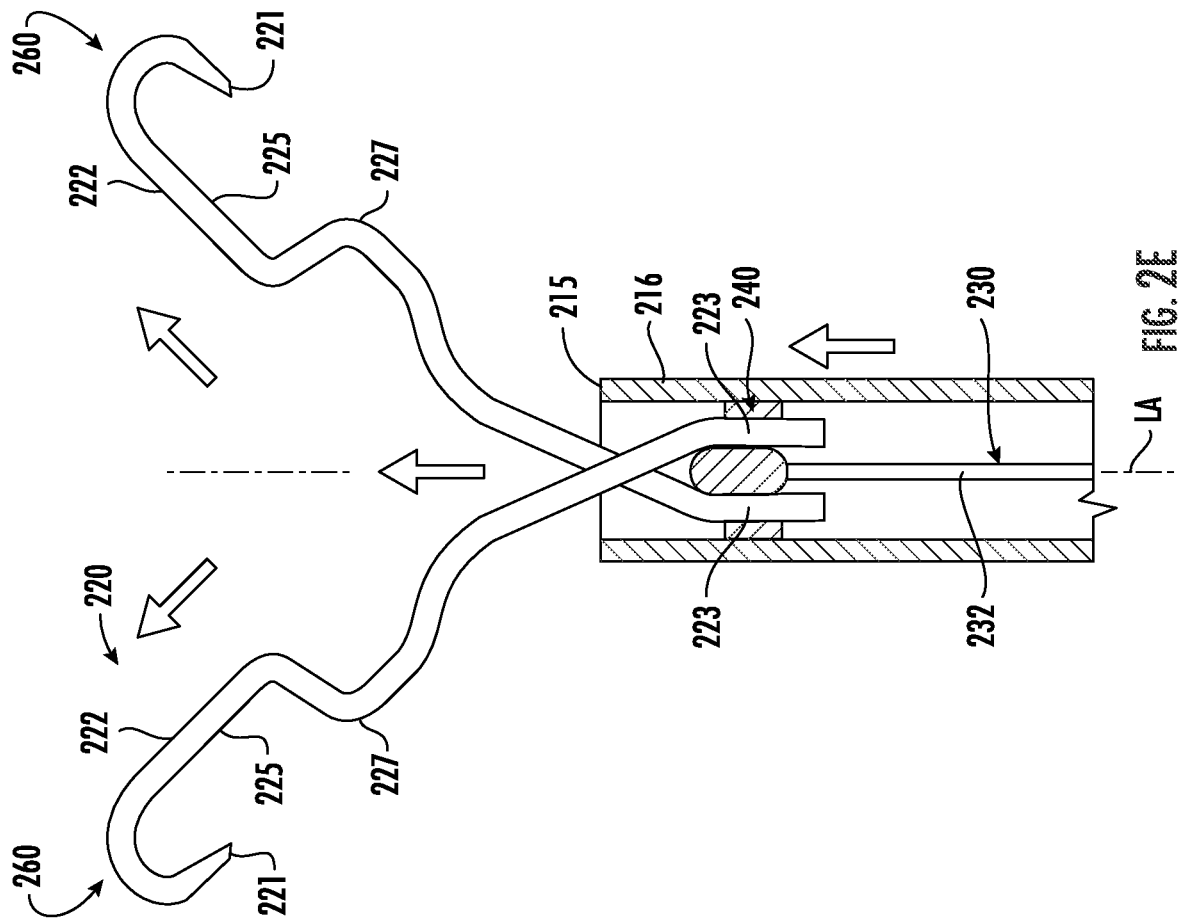
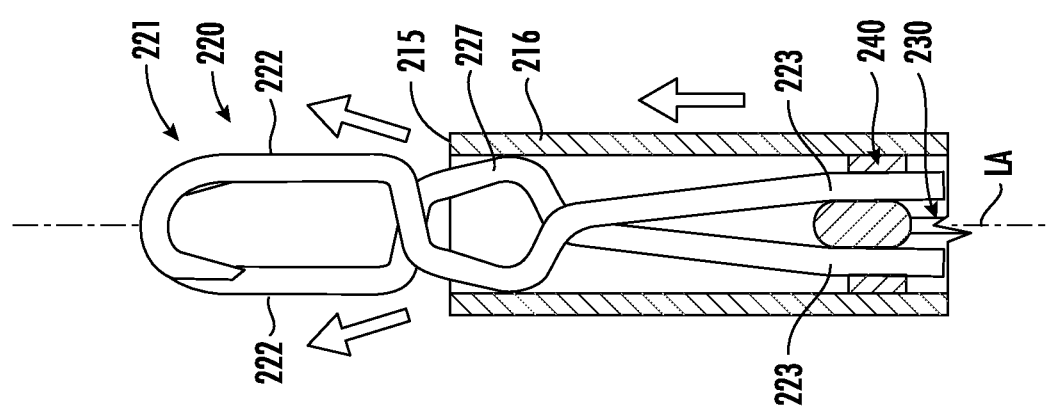

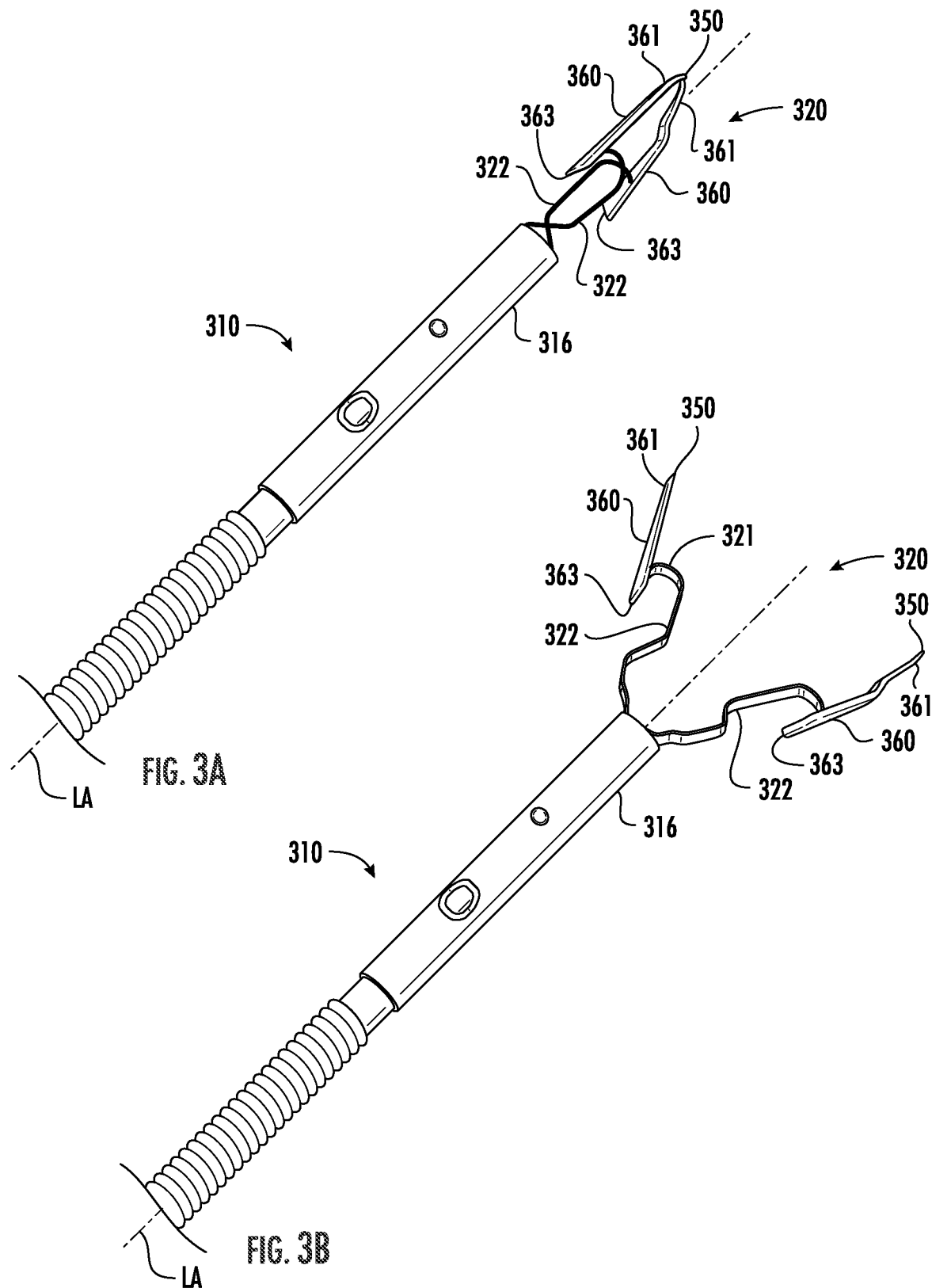

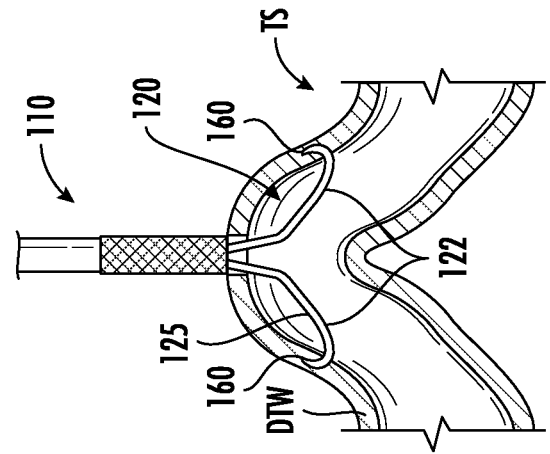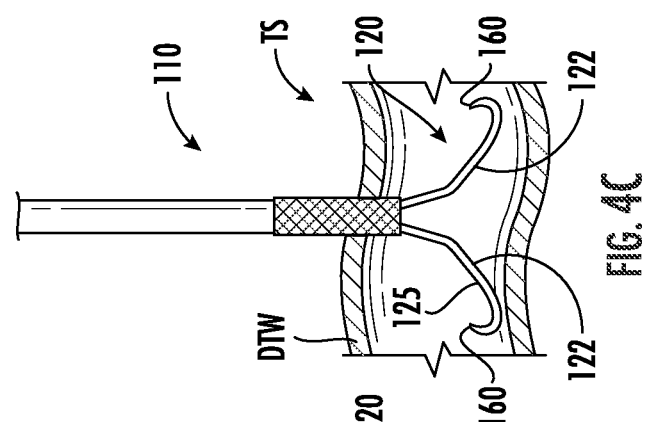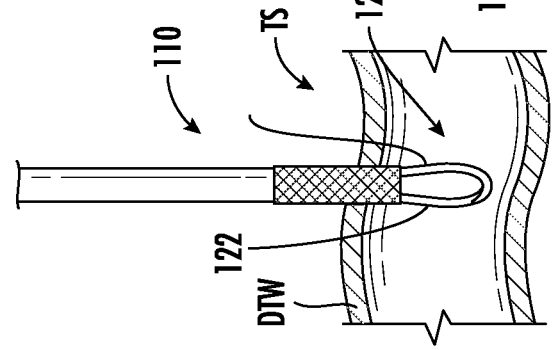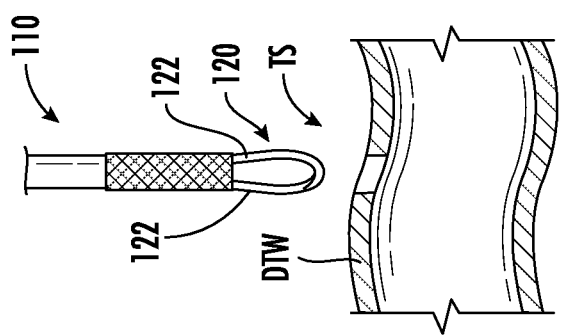

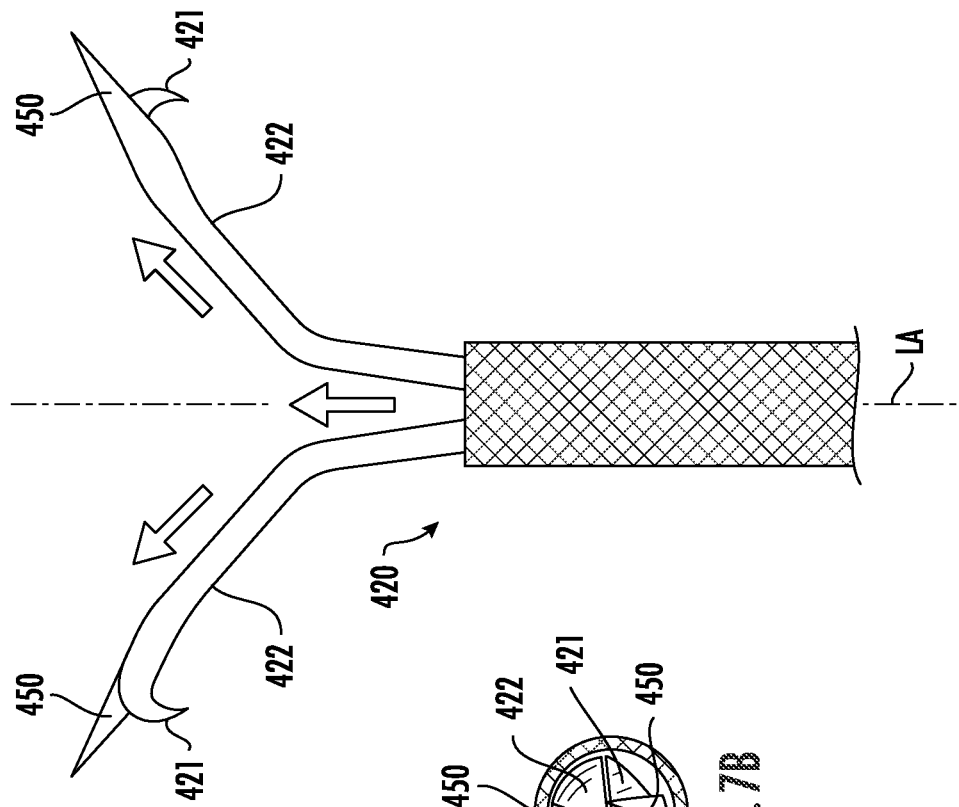
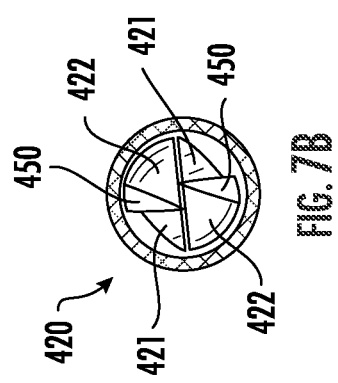
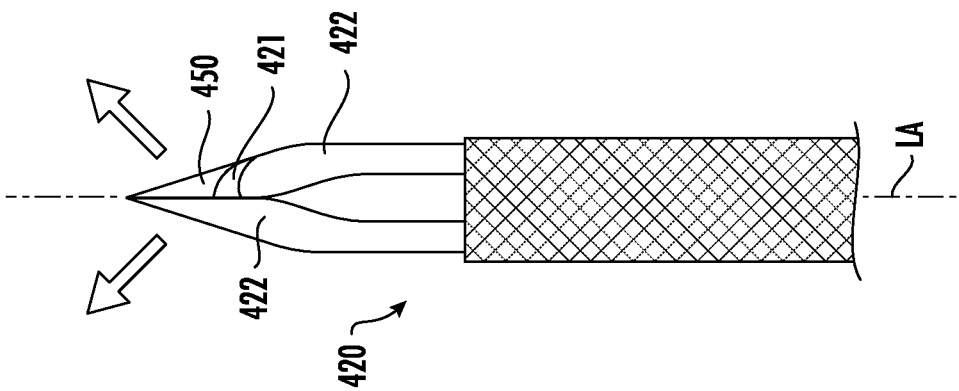
FIG. 7C
FIG. 7B
FIG. 7A

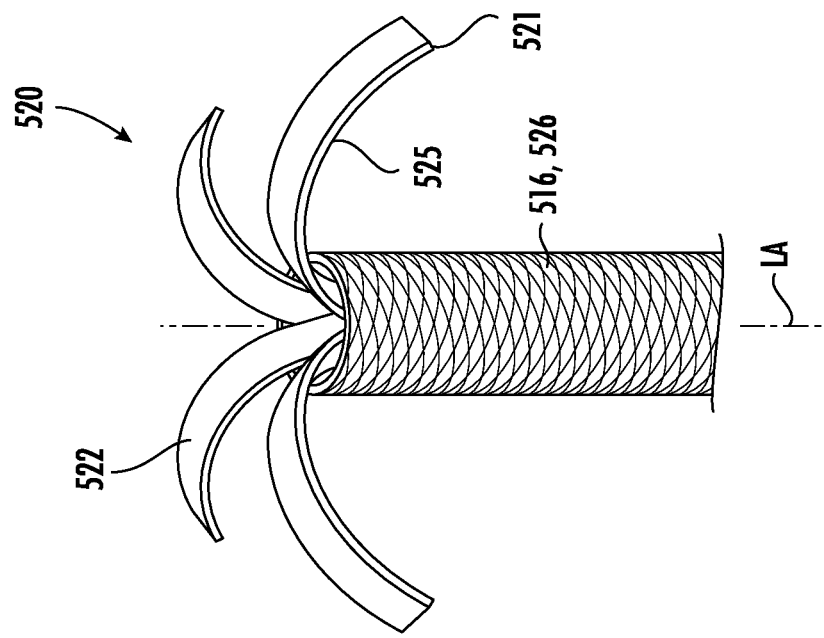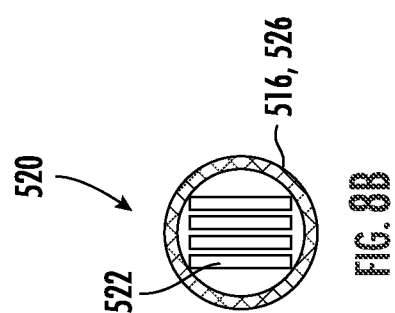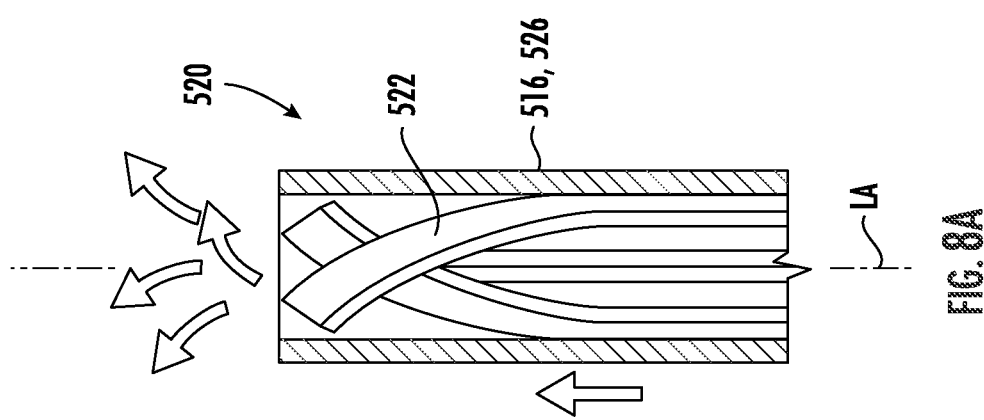

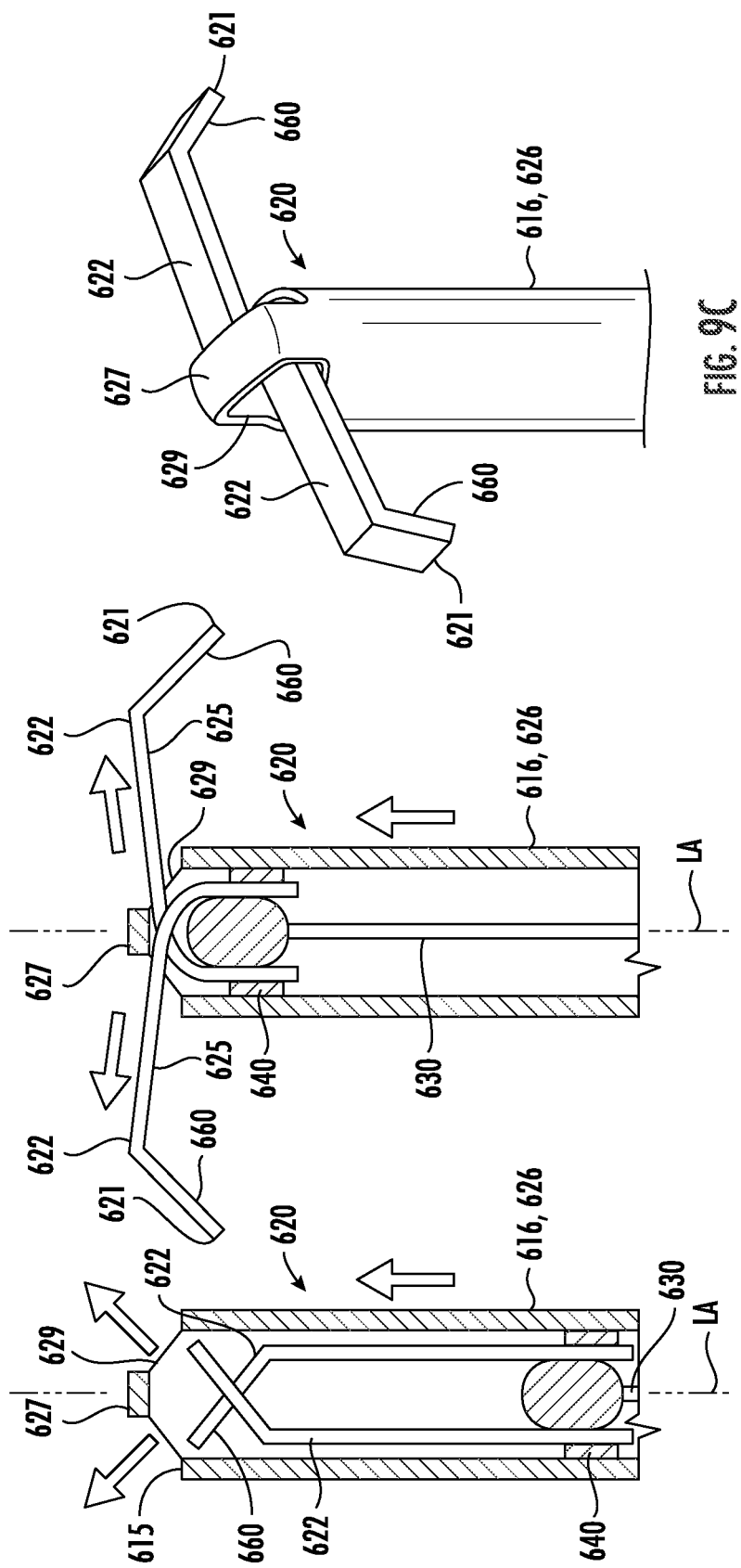

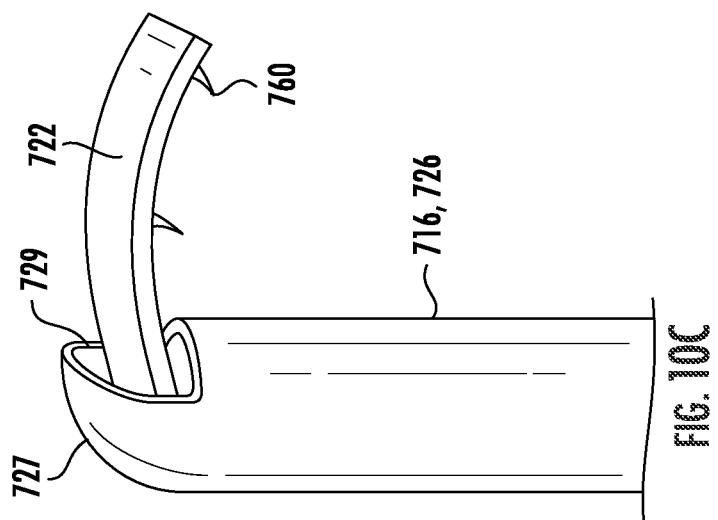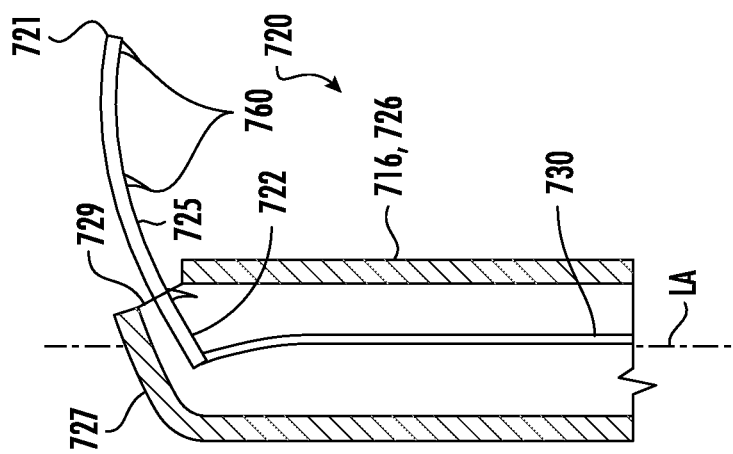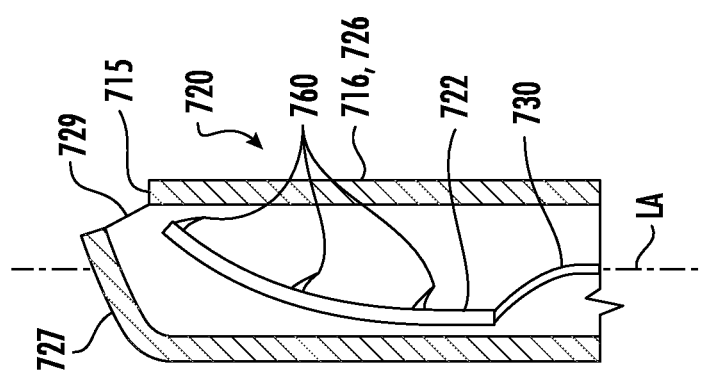

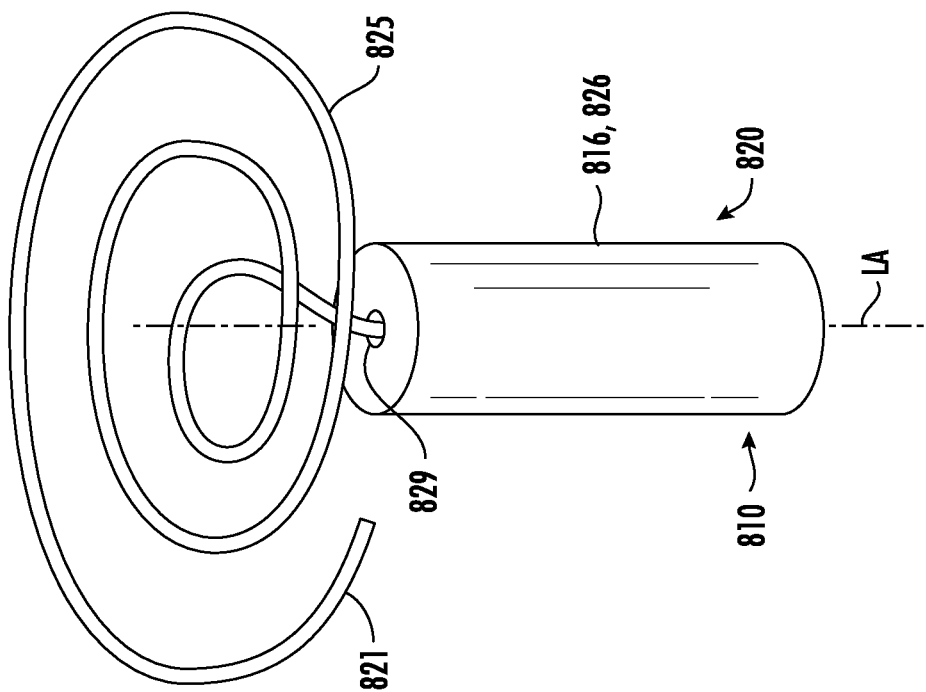
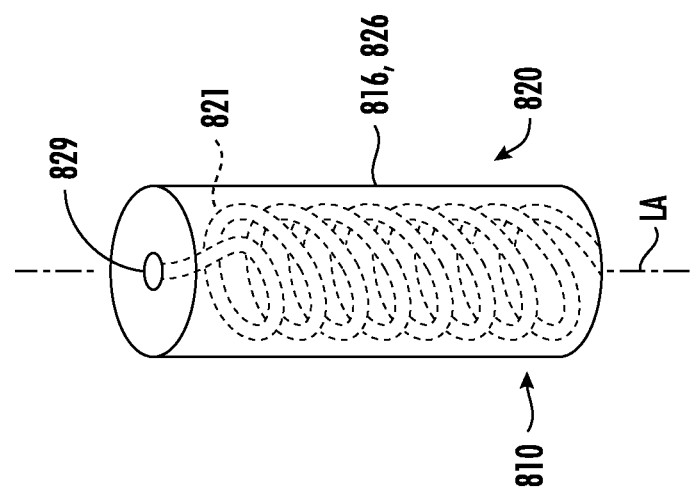

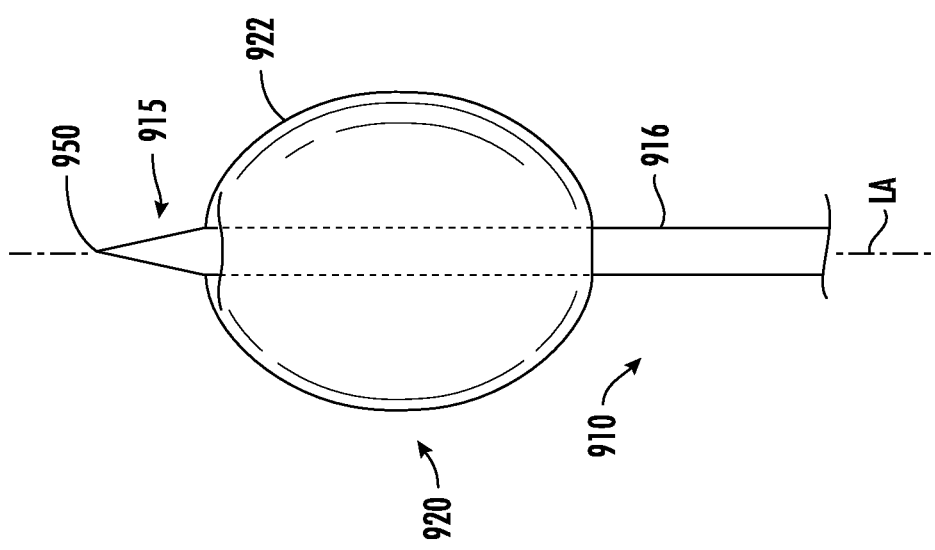
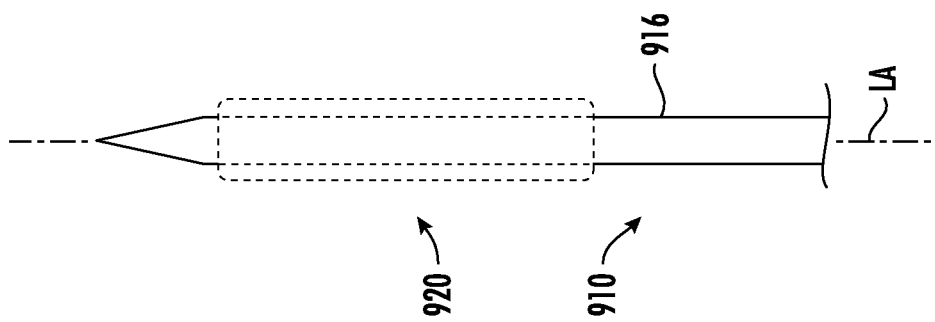

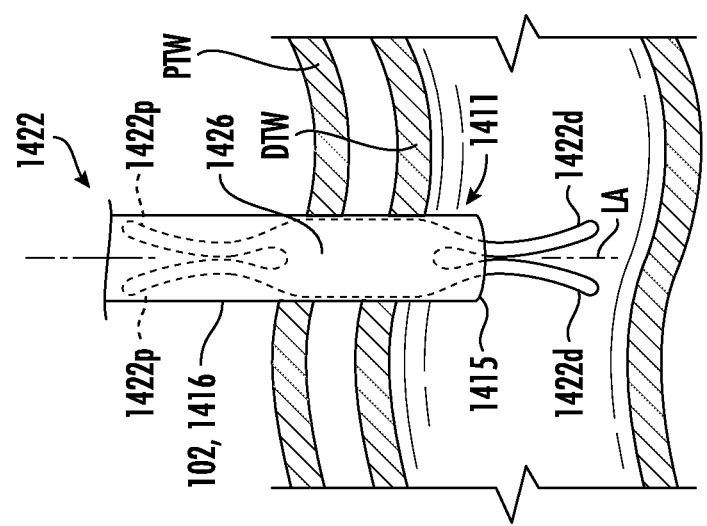
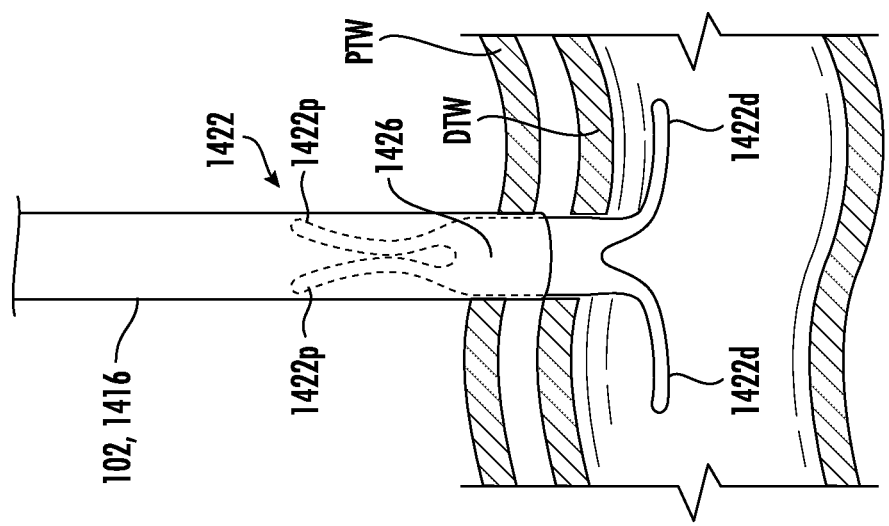
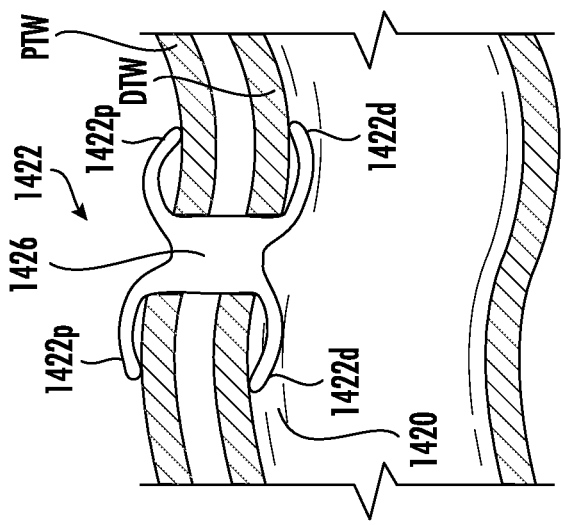
FIG. 20A
FIG. 20B
FIG. 20C

GRAPPLING SYSTEMS AND METHODS FOR LUMEN APPOSITION OR WOUND DEFECTS

PRIORITY

The present application is a non-provisional of, and claims the benefit of priority under 35 U.S.C. § 119 to U.S. Provisional Application Ser. No. 63/073,192, filed Sep. 1, 2020, the disclosure of which is hereby incorporated herein by reference in its entirety for all purposes.

FIELD

The present disclosure relates generally to apparatus and methods for manipulating a tissue wall and/or approximating tissue walls and/or maintaining tissue walls in apposition.

BACKGROUND

Tissue approximation is useful in many medical procedures for a variety of purposes. A number of medical procedures require a tissue wall (e.g., a body lumen wall or the wall of an organ) to be moved to a desired position, such as relative to another tissue wall to form an anastomosis between adjacent body lumens or to repair a body tissue. Challenges occur when moving a lumen towards another lumen and to anchor the two in place Improved tools, devices, systems, and methods for manipulating and moving body organs, tissues, lumens, and the like would thus be welcome in the medical field.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

The present disclosure is directed to a tissue-manipulating device and system capable of manipulating, grappling, grasping, approximating, drawing, pulling, holding, etc., (such terms being used interchangeably herein without intent to limit) tissue walls. Optionally, the device and system may be used to hold the tissue together in apposition. It is desirable to provide improved protocols and access and tissue-grasping/tissue-grappling tools, devices, and systems for drawing tissues together, such as for forming an anastomosis or repairing tissue. It is further desirable to provide protocols, tools, devices, and systems facilitating quicker methods for forming anastomoses. It is further desirable to provide protocols, tools, devices, and systems for holding tissue in apposition (such as while also minimizing any risk of leakage between the tissues).

In one aspect, the present disclosure relates to a tissue manipulating device comprising a shaft having a longitudinal axis, a tissue grasper assembly, and a controller. In some embodiments, the tissue grasper assembly comprises one or more resilient grasper arms expandable between a closed configuration extending within and along the longitudinal axis of the shaft, and an open configuration outside the shaft with the one or more grasper arms extending transversely away from the longitudinal axis of the shaft. In some embodiments, a grasper surface, is associated with at least one of the grasper arms, and is shaped and configured to engage a body tissue. In some embodiments, when the at least one grasper arm is in an open configuration and the grasper surface contacts a body tissue and the tissue-manipulating device is moved proximally, the tissue-manipulating device moves the body tissue proximally as well. In some embodiments, the controller is coupled to the tissue grasper assembly via a controller coupling and configured to move the grasper arms between the closed configuration and the open configuration.

In some embodiments, the grasper arms are resiliently biased in an open configuration in a radially outward direction away from the shaft when positioned outside the shaft.

In some embodiments, the grasper arms are resiliently held in an open configuration by a diverting feature formed on a distal end of the shaft.

In some embodiments, the tissue grasper assembly is separable from the shaft and the controller to remain deployed grasping body tissue. In some additional embodiment, the tissue grasper assembly comprises a locking feature engageable to hold the at least one grasper arm engaging tissue when the tissue grasper assembly is separated from the shaft and the controller. In some additional or alternative embodiments, the tissue-manipulating device further comprises a controller coupling coupled between the grasper arms and the controller, and movable upon actuation of the controller to move the at least one grasper arm between the closed configuration and the open configuration, the controller being separable from the controller coupling to deploy the tissue grasper assembly. In some alternative or additional embodiments, the tissue grasper assembly further comprises a capsule coupled to the shaft, the grasper arms being coupled to the shaft via the capsule, the tissue grasper assembly being separable with the capsule from the shaft and the controller to remain deployed grasping body tissue.

In some embodiments, at least one of the grasper arms includes a tissue grasping feature facing proximally toward the shaft when the grasper arms are extended distally outside the shaft and expanded into the open configuration.

In some embodiments, the tissue-manipulating device further comprises a sharpened element extending distally from a distal end of the tissue grasper assembly and configured for puncturing a body tissue wall.

In some embodiments, a grasper arm is in the form of a resiliently biased wire, and the grasper surface is a provided on a tissue retaining feature associated with the grasper arm.

In accordance with other aspects, the present disclosure relates to a tissue grasper assembly comprising a capsule having a longitudinal axis, one or more resilient grasper arms, and a controller coupling. In some embodiments, the one or more grasper arms are expandable between a closed configuration extending within and along the longitudinal axis of the capsule, and an open configuration outside the capsule with the one or more grasper arms extending transversely away from the longitudinal axis of the capsule. In some embodiments, a grasper surface is associated with at least one of the grasper arms, and is shaped and configured to engage a body tissue. In some embodiments, the controller coupling is coupled to at least one of the grasper arms and is movable to move the at least one grasper arm between the closed configuration and the open configuration.

In some embodiments, the tissue grasper assembly further comprises a locking feature engageable to hold the tissue grasper assembly in a configuration engaging tissue.

In some embodiments, the capsule is configured for coupling with a distal end of a shaft.

In some embodiments, the capsule has a proximal end and a distal end, and one or more grasper arms extend from each of the proximal end and the distal end of the capsule.

In some embodiments, the tissue grasper assembly further comprises a sharpened element extending distally from the tissue grasper assembly and configured for puncturing a body tissue wall.

In some embodiments, at least one of the grasper arms is resiliently held in an open configuration by a diverting feature formed on a distal end of said shaft.

In some embodiments, one or more of the grasper arms has a tissue grasping feature configured to engage tissue.

In accordance with other aspects, the present disclosure relates to a method of manipulating tissue with a tissue-manipulating device, the method comprising extending a tissue-manipulating device, comprising a shaft with a longitudinal axis and a tissue grasper assembly, through a distal tissue wall to move a distal end of the tissue-manipulating device distal to the distal tissue wall, actuating a tissue-manipulating device controller, and moving the tissue-manipulating device proximally to move the distal tissue wall proximally. In some embodiments, the tissue grasper assembly comprises at least one resiliently extendable grasper arm in a closed configuration extending within and along the shaft when the tissue-manipulating device is extended through the distal tissue wall. In some embodiments, actuating the tissue-manipulating device controller comprises extends the at least one resiliently extendable grasper arm from inside the shaft to outside the shaft to allow the at least one resiliently extendable grasper arm to expand into an open configuration extending transverse to the longitudinal axis of the shaft. In some embodiments, moving the tissue-manipulating device proximally engages the at least one grasper arm with the distal tissue wall and to move the distal tissue wall proximally.

In some embodiments, the method further comprises extending the tissue-manipulating device through a proximal tissue wall before extending the tissue-manipulating device through the distal tissue wall, and moving the tissue-manipulating device proximally to move the distal tissue wall in apposition to the proximal tissue wall.

In some embodiments, the method further comprises separating the tissue grasper assembly from the shaft to deploy the tissue grasper assembly holding the proximal tissue wall and the distal tissue wall in apposition.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows:

FIG. 2A is an elevational view of a tissue-manipulating device formed in accordance with principles of the present disclosure and shown in a closed configuration for delivery to a treatment site.

FIG. 2B is an end view of the tissue-manipulating device of FIG. 2A.

FIG. 2C is an elevational view of a tissue-manipulating device as in FIG. 2A in an open configuration for manipulating tissue.

FIG. 2D is an elevational view of another embodiment of a tissue-manipulating device in a closed configuration according to the present disclosure.

FIG. 2E is an elevational view of the tissue manipulating device of FIG. 2D in an open configuration.

FIG. 3A is a perspective view of another tissue-manipulating device formed in accordance with principles of the present disclosure and shown in a closed configuration for delivery to a treatment site.

FIG. 3B is a perspective view of the tissue-manipulating device as in FIG. 3A in an open configuration for manipulating tissue.

FIGS. 4A-4D illustrate sequential positions of a tissue-manipulating device formed in accordance with principles of the present disclosure with respect to tissues to be moved into apposition.

FIG. 7A is an elevational view of a tissue-manipulating device formed in accordance with principles of the present disclosure and shown in a closed configuration for delivery to a treatment site.

FIG. 7B is an end view of the tissue-manipulating device of FIG. 7A.

FIG. 7C is an elevational view of a tissue-manipulating device as in FIG. 7A or FIG. 7B in an open configuration for manipulating tissue.

FIG. 8A is an elevational view of a tissue-manipulating device formed in accordance with principles of the present disclosure and shown in a closed configuration for delivery to a treatment site.

FIG. 8B is an end view of the tissue-manipulating device of FIG. 8A.

FIG. 8C is an elevational view of a tissue-manipulating device as in FIG. 8A or FIG. 8B in an open configuration for manipulating tissue.

FIG. 9A is an elevational view of a tissue-manipulating device formed in accordance with principles of the present disclosure and shown in a closed configuration for delivery to a treatment site.

FIG. 9B is an elevational view of a tissue-manipulating device as in FIG. 9A in an open configuration for manipulating tissue.

FIG. 9C is a perspective view of a tissue-manipulating device as in FIG. 9A or FIG. 9B in an open configuration for manipulating tissue.

FIG. 10A is an elevational view of a tissue-manipulating device formed in accordance with principles of the present disclosure and shown in a closed configuration for delivery to a treatment site.

FIG. 10B is an elevational view of a tissue-manipulating device as in FIG. 10A in an open configuration for manipulating tissue.

FIG. 10C is a perspective view of a tissue-manipulating device as in FIG. 10A or FIG. 10B in an open configuration for manipulating tissue.

FIG. 11A is a perspective view of a tissue-manipulating device formed in accordance with principles of the present disclosure and shown in a closed configuration for delivery to a treatment site.

FIG. 11B is a perspective view of a tissue-manipulating device as in FIG. 11A in an open configuration for manipulating tissue.

FIG. 12A is an elevational view of a tissue-manipulating device formed in accordance with principles of the present disclosure and shown in a closed configuration for delivery to a treatment site.

FIG. 12B is an elevational view of a tissue-manipulating device as in FIG. 12A in an open configuration for manipulating tissue.

FIGS. 20A-20C illustrate sequential positions of a tissue-manipulating device formed in accordance with principles of the present disclosure with respect to tissues to be moved into apposition.

DETAILED DESCRIPTION

Figure 1:
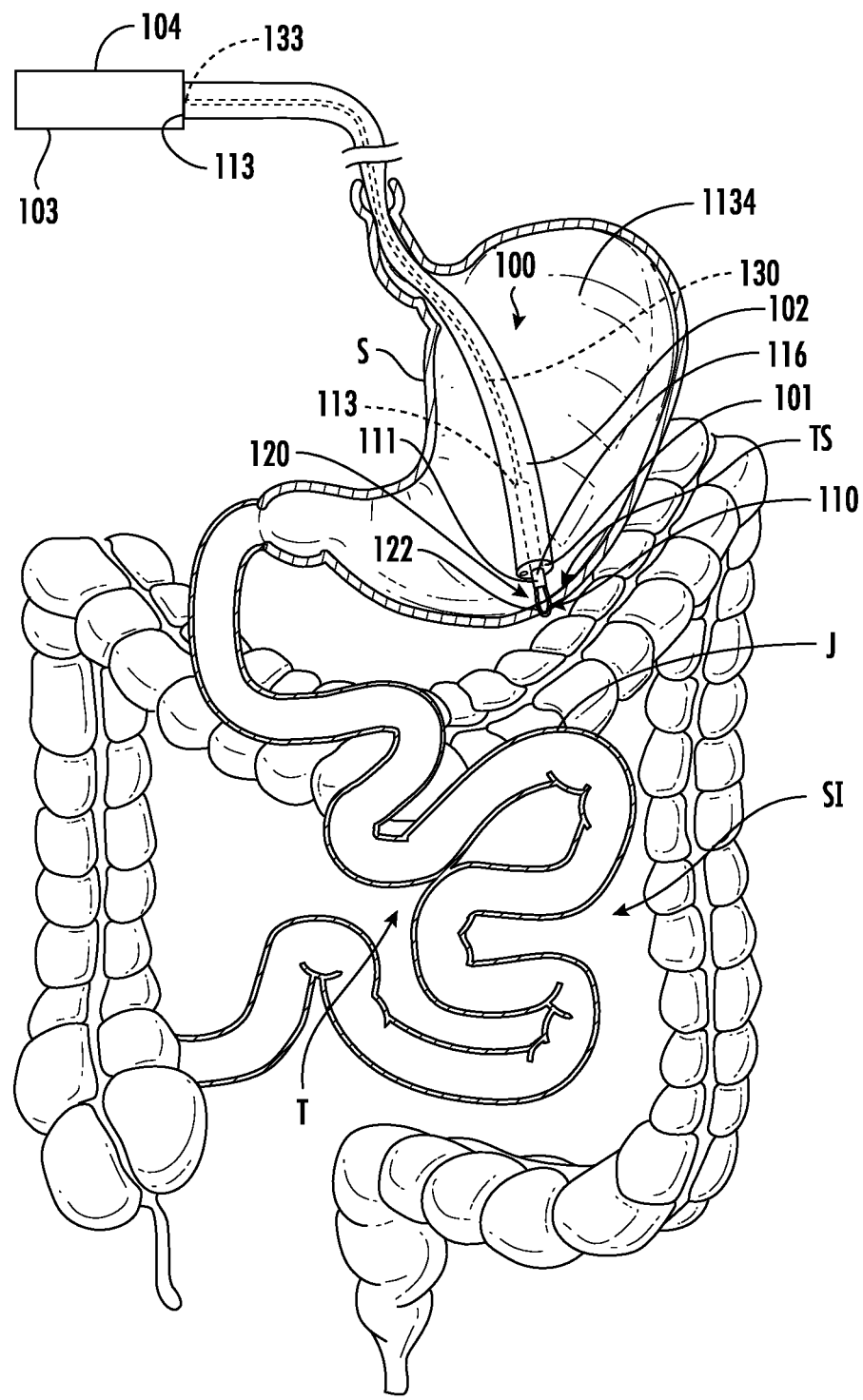
FIG. 1 illustrates a human gastrointestinal system as an example environment in which embodiments of the present disclosure may be applied or used or deployed.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably without intent to limit or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a channel, or a bore.

As will now be described with reference to the drawings, devices and systems and methods are disclosed herein for manipulating a tissue wall and/or approximating tissue walls and/or maintaining tissue walls in apposition at a treatment site. The medical devices, instruments, tools, etc. of the present disclosure are not limited, and may include a variety of medical devices for accessing body passageways, including, for example, duodenoscopes, catheters, ureteroscopes, bronchoscopes, colonoscopes, arthroscopes, cystoscopes, hysteroscopes, and the like. It should be appreciated that reference will be made herein to manipulating and/or other terms, such as grappling, grasping, approximating, drawing, pulling, holding, etc., such terms being used interchangeably herein without intent to limit. Tissue wall, such as, without limitation, organ or lumen walls, may be drawn closer together or to another tissue wall, such as to hold the tissue walls in apposition, such as to form an anastomosis. For instance, the device and system may engage and pull a portion of a small intestine toward a stomach wall, such as by puncturing through the walls of the small intestine and stomach, and hold the lumens/tissues together. Such methods and apparatus can also be used for access to and from portions of the urinary tract, such as the urinary bladder and ureter, the pulmonary tract, such as the trachea and bronchi, and the biliary tract, such as the bile duct and gallbladder, and vascular applications, as well. Alternatively, separated ends of tissue wall may be drawn together to close a defect therebetween. It will be appreciated that the present disclosure should not be interpreted as being limited to such procedures or end results. Moreover, although reference is made to a treatment site, such reference is merely for the sake of convenience and not intended to limit the scope of the disclosure.

In accordance with various principles of the present disclosure, the distal end of a tissue-manipulating device has an elongate member which generally is hollow, such as a catheter, a cannula, a hollow shaft, etc. (referenced herein as a shaft for the sake of simplicity and without intent to limit), through which one or more grasper arms may be extended. In some embodiments the shaft is in the form of a collar or capsule. In some embodiments, the shaft includes a collar or capsule (such terms being used interchangeably herein without intent to limit) formed separately from the shaft and coupled thereto, and optionally removable from the shaft for deployment of the tissue grasper assembly (including the grasper arms) of the tissue-manipulating device. The grasper arms are movable between a closed configuration within the shaft (and generally extending within a lumen defined within the shaft and along the longitudinal or axial extent of the lumen and shaft), and an open configuration in which the grasper arms expand or extend away from the shaft, such as to engage tissue wall. In some embodiments, the grasper arms are resiliently biased, such as to be held in an open configuration capable of engaging tissue. In some embodiments, the grasper arms are resiliently biased to expand or otherwise to extend into an open configuration upon release or deployment from the shaft. In other embodiments, another element of the tissue manipulating device may hold the resiliently biased grasper arms in an open configuration.

The tissue-manipulating device may be advanced to a treatment site through a working channel of a delivery device, such as a flexible elongate member (e.g., a catheter, endoscope, cannula, delivery shaft, etc., the term flexible elongate member being used herein to refer to the delivery device in general for the sake of convenience and without intent to limit), of a tissue-manipulating system. The grasper arms may be controlled (e.g., advanced beyond a distal end of the shaft and into the second configuration to engage tissue) by a tissue-manipulating device controller extending along (e.g., through, or outside and along) the flexible elongate member from a proximal end of the flexible elongate member to the distal end of the flexible elongate member. The distal end of the tissue-manipulating device controller is coupled with or engages at least one grasper arm to control movement of the grasper arm as desired or indicated by the procedure with which the tissue-manipulating device is used. The proximal end of the tissue-manipulating device controller may be engaged with or coupled to or otherwise associated with a control handle associated with the tissue-manipulating system and facilitating actuation of the tissue-manipulating device controller as well as other components of the tissue-manipulating system. Any of a variety of control handles known or heretofore known in the art may be used to manipulate the tissue-manipulating device controller (as well as other components or structures of the tissue-manipulating system), such as via the proximal end thereof, the particular details of the configuration not limiting the scope of the present disclosure. In some embodiments, the tissue-manipulating device controller may be distally advanced or proximally retracted to manipulate the positions of the grasper arms relative to the shaft to cause the grasper arms to move between the closed configuration and the open configuration.

Various features may be provided to facilitate grasping, grappling, moving, etc. (such terms being used interchangeably herein without intent to limit) the tissue. In accordance with some embodiments described herein, at least one of the grasper arms may be shaped and configured to enhance engagement and/or grasping of tissue. In some embodiments, the free ends (e.g., distal ends) of at least one of the grasper arms is shaped and configured to enhanced engagement and/or grasping of tissue, such as by latching onto the tissue. In some embodiments, one or more tissue grasping features, such as hooks, are provided along one or both of the grasper arms between the attached end (the end coupled to the rest of the tissue-manipulating device, such as a proximal end of the grasper arms) and the free end of the grasper arm.

In accordance with some embodiments disclosed herein, the distal end of the tissue-manipulating device may be configured to facilitate passage thereof through tissue walls to be manipulated. In some embodiments, the distal end of the tissue-manipulating device is provided with a sharp end, such as a needle or other sharpened element, capable of puncturing tissue walls. In some embodiments, the sharp end may be associated with the shaft and/or grasper arms.

In accordance with some embodiments disclosed herein, the grasper arms may be coupled to a tissue grasper assembly configured to be releasable from the tissue-manipulating device controller for deployment with the tissue grasper assembly maintaining the approximated tissues in apposition to each other. Additional embodiments of tissue graspers which may be deployed and left in place to hold together tissue (e.g., bringing together walls of different organs or lumens, or repairing a defect and holding together the tissue surrounding the defect) are also disclosed.

Various embodiments of tissue-manipulating devices, systems, and methods will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

Turning now to the drawings, a tissue-manipulating system 100 formed in accordance with principles of the present disclosure is illustrated in a schematic representation of a gastrointestinal system, such as to create an anastomosis between a stomach S and a portion of the small intestine SI, such as the jejunum J. It will be appreciated that the gastrointestinal system is simply one of a number of anatomical sites in which a tissue-manipulating system 100 formed in accordance with principles of the present disclosure may be used, the particular anatomical site not affecting the scope of the present disclosure or limiting the disclosed tissue-manipulating system 100. The tissue-manipulating system 100 may include a delivery device, such as a flexible elongate member 102, such as an endoscope, cannula, delivery shaft, etc., (the term flexible elongate member being used herein to refer to the delivery device in general for the sake of convenience and without intent to limit) having a working channel therethrough via which a tissue-manipulating device 110 is guided to a treatment site TS. The tissue-manipulating device 110 includes a tissue grasper assembly 120 at a tissue-manipulating device distal end 111 configured to engage tissue to be manipulated by the tissue-manipulating device 110. A tissue-manipulating device controller 130 (shown schematically in phantom lines extending through the flexible elongate member 102) extends from the tissue grasper assembly 120 to a proximal end 113 of the tissue-manipulating device 110 for access and manipulation by the user (e.g., medical professionals, such as physicians, technicians, endoscopists, etc., and/or automated system or otherwise) to control the tissue grasper assembly 120. The tissue-manipulating device 110 may be arranged with respect to the tissue-manipulating system 100 such that the tissue grasper assembly 120 extends from a distal end 101 of the tissue-manipulating system 100, and such that a proximal end 133 of the tissue-manipulating device controller 130 is positioned at or along a proximal end 103 of the tissue-manipulating system 100. A control handle 104 may be provided at a proximal end 103 of the tissue-manipulating system 100 and may be associated with the tissue-manipulating device controller 130 and/or a controller of the flexible elongate member 102 (any controller known or heretofore known in the art and not illustrated as not necessary for a complete understanding of the tissue-manipulating device 110).

The tissue-manipulating device 110 is configured to be delivered through the flexible elongate member 102 to a treatment site TS in accordance with known or heretofore known techniques for advancing devices or systems through a patient's anatomy to a treatment site TS. The distal end 111 of the tissue-manipulating device 110 may have profile configured to readily pass through an opening through a proximal tissue wall and a distal tissue wall, such as may be appreciated with reference to various embodiments of tissue-manipulating devices and tissue grasper assemblies disclosed herein (see, e.g., FIG. 2). The distal end 111 of the tissue-manipulating device 110 may be configured so as to readily pass through aperture or passage designated for (e.g., created for passage of or created by, as discussed in further detail below) the tissue-manipulating device 110 without creating any unwanted damage (e.g., abrasions, lacerations, tears, etc.). In some embodiments, the distal end 111 of the tissue-manipulating device 110 is configured to puncture the tissue walls and then pass therethrough, as described in further detail below.

In accordance with one aspect of disclosure, the tissue grasper assembly 120 includes one or more grasper arms 122 carried by the shaft 116, such as through the flexible elongate member 102, for delivery to the treatment site TS. The grasper arms 122 may be delivered in a closed configuration stored within the shaft 116 and with a sufficiently low profile to move distally through the tissue-manipulating system 100. The tissue-manipulating device controller 130 is actuatable (e.g., movable) to actuate the tissue grasper assembly 120 to cause the grasper arms 122 to move from a closed configuration to an open configuration in which the grasper arms 122 are expanded and/or extend away from the shaft 116 to provide a grasper surface configured and shaped and with sufficient surface area to engage with tissue to be manipulated. In some embodiments, the tissue-manipulating device controller 130 is moved distally or proximally to actuate the grasper arms 122. However, other movements or control of the tissue-manipulating device controller 130 are within the scope of the present disclosure, the particular movements not being critical to the broad principles of the disclosure.

An example of an embodiment of a tissue grasper assembly 220 formed in accordance with various principles of the present disclosure is illustrated in FIGS. 2A-2C. The illustrated tissue grasper assembly 220 has one or more grasper arms 222 shown in FIG. 2A and FIG. 2B in a closed configuration at least partially held within the shaft 216 for delivery to a treatment site TS. If desired, the grasper arms 222 may be shaped and configured to assume a compact configuration within the lumen 217 of the shaft 216, such as may be appreciated with reference to FIG. 2B. In some embodiments, as illustrated in FIG. 2A, the distal ends 221 of the grasper arms 222 may extend distally outwardly from a distal end 215 of the shaft 216 as the tissue-manipulating device 210 is advanced to the treatment site TS. If desired, a sharpened element, such as a sharpened element as illustrated in FIGS. 7A-7C and described in further detail below, may be provided on (e.g., formed separately and coupled to, or formed as a part of or extension of) the distal ends 221 of the grasper arms 222 for use in puncturing a tissue wall to allow the tissue grasper assembly 220 to pass therethrough. Alternatively, if the distal ends 221 of the grasper arms 222 do not extend distally from the distal end 215 of the shaft 216, the sharpened element 150 may be provided or formed on the distal end 215 of the shaft 216. Provision of such sharpened element on the tissue grasper assembly 220 may facilitate the tissue manipulating procedure, such as by reducing operations and/or necessary instruments or devices. If a sharpened element is not provided, the opening through the tissue walls through which the tissue grasper assembly 220 is passed may be preformed in the tissue walls (such as by a separate cutting instrument) prior to insertion of the tissue grasper assembly 220 therethrough.

The grasper arms 222 of the tissue grasper assembly 220 of FIGS. 2A-2C are movable or extendable or expandable (such terms being used interchangeably herein without intent to limit) from the closed configuration of FIG. 2A to an open configuration, such as illustrated in FIG. 2C, in which the grasper arms 222 extend or expand outwardly (e.g., radially outwardly or otherwise transverse to a longitudinal axis L of the shaft 216 or tissue grasper assembly 220) from the shaft 216/tissue grasper assembly 220. In accordance with one aspect of the present disclosure, the grasper arms 222 are resiliently biased to expand or otherwise to extend into the open configuration (e.g., extending away from the shaft 216) for engaging tissue to be manipulated. In some embodiments, such as the embodiment of FIGS. 2A-2C, the grasper arms 222 are formed of a shape memory material (e.g., stainless steel or a memory shape alloy, such as Nitinol) and the grasper arms 222 are shaped and configured to be biased towards an open configuration extending away from the longitudinal axis L of the shaft 216 or tissue grasper assembly 220. When the grasper arms 222 are in a stored configuration within the shaft 216, the shaft 216 holds the grasper arms 222 in a closed configuration against the natural bias of the grasper arms 222. In some embodiments, the grasper arms 222 include a knuckle or other bend or diverting feature 227 shaped and configured and positioned to hold the grasper arms 222 in a compact configuration within the shaft 216, such as by pressing against the interior of the shaft 216 to bias the grasper arms 222 into a compact closed configuration within the shaft 216. In some embodiments, the grasper arms 222 cross each other when in a closed configuration and move past each other to expand or extend into the open configuration, as may be appreciated with reference to FIGS. 2D and 2E. Once the grasper arms 222 are distally extended out of the shaft 216, the grasper arms 222 may expand or extend into the open configuration illustrated in FIG. 2C.

In one embodiment, the grasper arms 222 are movable by actuating a tissue-manipulating device controller 230. The tissue-manipulating device controller 230 is coupled to the grasper arms 222 and extends proximally, such as to the proximal end 113 of the tissue-manipulating device 110 and/or the proximal end 103 of the tissue-manipulating system 100 as illustrated in FIG. 1, for access by a user to actuate the tissue-manipulating device controller 230 to operate the grasper arms 222 to move as desired (e.g., relative to the shaft 216) such as between closed and open configurations. The tissue-manipulating device controller 230 may be coupled to the grasper arms 222 with a controller coupling 240 known or heretofore in the art capable of transmitting the desired control movements or actions from the tissue-manipulating device controller 230 to the grasper arms 222. The controller coupling 240 preferably holds the proximal ends 223 of the grasper arms 222 in place while allowing flexing or other movement (e.g., radially outward movement or expansion) of the grasper arms 222. The controller coupling 240 may seat inside windows or cut-outs or grooves within shaft 216 to inhibit or to lock the grasper arms 222 in a desired configuration. An additional collar or stop on a proximal end 213 of the shaft 216 may be provided to create a hard stop for the controller coupling 240. Additionally or alternatively, frictional forces or specific geometries (interengaging) of the grasper arms 222 and controller coupling 240 and/or shaft 216 may cause desired binding of the system to hold the grasper arms 222 in the desired place or configuration. Other configurations, such as bayonet locks or barbs other elements, are within the scope of the present disclosure.

The tissue-manipulating device controller 230 may, in some embodiments, include a controller element 232 in the form of a wire or other element or structure known or heretofore known in the art capable of moving the grasper arms 222 with respect to the shaft 216. The controller element 232 may be capable of extending to or being coupled with an additional controller element at the proximal end 103 of the tissue-manipulating system 100 for operation or control by a user, such as via a control handle 104 at the proximal end 103 of the tissue-manipulating system 100. The controller element 232 is illustrated as being coupled or otherwise engaged with the controller coupling 240. Movement of the controller element 232 (e.g., distal or proximal translation of the controller element 232) imparts movement to the tissue grasper assembly 220 to cause the grasper arms 222 to move between the closed and open configurations. It will be appreciated that other configurations of a tissue-manipulating device controller and a controller coupling are within the scope and spirit of the present disclosure, operation and movement of the grasper arms not being limited by a particular configuration of controller or controller coupling.

In the open configuration, the grasper arms 222 present a grasper surface 225 preferably shaped and configured and having sufficient surface area to engage tissue to allow movement of the grasper arms 222 to manipulate the tissue. In some embodiments, as illustrated in FIG. 2C, the free end 221 (as used herein, a "free end" of an element is a terminal end at which such element does not extend beyond) of at least one of the grasper arms 222 is provided with a tissue grasping feature 260 configured to facilitate grasping or engagement of tissue, such as a barb or hook or jaws or other tissue-engaging projection. The tissue grasping feature 260 is configured to enhance grasping of tissue so that the grasper arms 222 do not inadvertently move with respect to the tissue wall being manipulated, or tissue walls held in place by a tissue grasper assembly 220 deployed and left in place for such function (such as to keep apposed tissues of different organs or lumens together, or to keep tissue surrounding a defect together to repair the defect, as described in further detail below). For instance, the tissue grasping feature 260 may hold the grasper arms 222 against lateral shifting with respect to the engaged tissue. In the embodiment illustrated in FIG. 2C, the tissue grasping feature 260 is in the form of curved jaws with distally-facing tips to improve grasping. However, other configurations, locations, etc., including but not limited to other configurations and locations disclosed herein, may be substituted for the illustrated tissue grasping feature 260 configuration. It will be appreciated with reference to FIGS. 2A and 2C that the grasper arms 222 may be curved such that in a closed configuration the grasper arms 222 are positioned with the concave curved sides or surfaces facing each other to present a convex (e.g., atraumatic) surface at the distal end 221 of the tissue grasper assembly 120. Upon moving to the open configuration, the grasper arms 222 move across each other and away from the longitudinal axis LA to present the convex curved sides distally so that the concave curved sides face the treatment site TS with the tissue grasping feature 260 positioned to engage the tissue at the treatment site TS.

An alternative embodiment of a tissue grasper assembly 320 with grasper arms 322 including one or more tissue grasping features 360 is illustrated in FIGS. 3A and 3B. As may be appreciated, the illustrated tissue grasping features 360 are at respective distal ends 321 of respective grasper arms 322 and may be wider than the distally-extending portions of the respective grasper arms 322 from which the tissue grasping features 360 extend. In such a configuration, the tissue grasping features 360 have proximally-facing tissue-engaging ends 363 (blunt or sharp, but not sharp enough to puncture or cut tissue) configured and positioned to engage or contact or grasp tissue at a treatment site TS when the tissue-manipulating device 310 is moved proximally with the grasper arms 322 in the open configuration illustrated in FIG. 3B. The tissue-engaging ends 363 may be configured to facilitate latching onto or otherwise engaging with the tissue at the treatment site TS. Further proximal movement of the tissue-manipulating device 310 moves or manipulates the engaged tissue proximally with the tissue-manipulating device 310. In some embodiments, as illustrated, the tissue grasping features 360 may include a sharpened element 350 such as a sharpened area of (or sharpened element coupled to) the distal end 361 of the tissue grasping feature 360, such as to puncture tissue wall to gain access as described above with respect to other embodiments of sharpened elements on distal ends of grasper arms or shafts.

In some embodiments, a tissue grasping feature is provided in a configuration which contacts or engages tissue to move the tissue upon movement of the tissue grasper assembly and tissue-manipulating device, but is not otherwise inhibited or restricted from shifting (e.g., moving laterally) with respect to the engaged tissue. Such tissue grasping feature may be said to contact or abut the engaged tissue without latching into the tissue or otherwise engaging the tissue in a manner which allows the tissue grasping feature alone to grasp the tissue (e.g., as with a hook or barb or the like, which latches into tissue and which may thereby grasp the tissue independently of further movement or features of the grasper arms). In some instances of such embodiments, the tissue grasping feature is in the form of a blunt or smooth surface, such as a surface which does not latch into the tissue. In some further instances of such embodiments, the grasper arms have a grasper surface with an increased surface area as compared with the surface area of regions or sections of the grasper arms distal to such tissue grasping feature and/or as compared with a tissue grasping feature which may grasp tissue independently of other features or movement of the grasper arms (e.g., by latching into the tissue).

Examples of manipulations and movements of a tissue-manipulating device 110 formed in accordance with principles of the present disclosure, in use in accordance with some aspects of the present disclosure, are illustrated in FIGS. 4A-4D, 5A-5C, and 6A-6C. Although the illustrated tissue-manipulating device 110 may resemble the tissue-manipulating device 210 of FIGS. 2A-2E, it will be appreciated that the examples of FIGS. 4A-4D, 5A-5C, and 6A-6C are not limited to a particular configuration of a tissue-manipulating device, and other configurations, such as disclosed herein or otherwise, may be used instead.

As illustrated in FIG. 4A, a tissue-manipulating device 110, illustrated in a closed configuration, has already been advanced distally through a distal end of a delivery device (such as a flexible elongate member 102, if used, as illustrated in FIG. 1), optionally through a proximal body cavity or lumen (not shown), and is illustrated as approaching a treatment site TS, such as a distal tissue wall DTW. The opening through the distal tissue wall DTW through which the tissue grasper assembly 120 is passed may be preformed (such as by a separate cutting procedure) in the tissue walls prior to insertion of the tissue grasper assembly 120 therethrough. Alternatively, if a sharpened element is provided on the distal end 101 of the tissue-manipulating device 110, the sharpened element may create the opening, such as by puncturing the distal tissue wall DTW with the sharpened element. In FIG. 4B, the tissue-manipulating device 110 is illustrated extended through a distal tissue wall DTW (e.g., an organ wall, such as a stomach wall, or a lumen wall distal to the proximal body cavity or lumen), and into a distal body cavity or lumen. In FIG. 4C, the tissue grasper assembly 120 is shown moving or having been moved into an open configuration (such as by operation of the tissue-manipulating device controller 130, not shown in this illustration). The tissue grasper assembly 120 is then moved proximally to engage the distal tissue wall DTW (e.g., with the grasper arms 122 such as with a tissue grasper surface 125 and/or a tissue grasping feature 160 formed on one or more of the grasper arms 122). As illustrated in FIG. 4D, the distal tissue wall DTW may then be manipulated as desired such as to a desired location, such as proximally (for instance, a distal lumen may be moved proximally) towards and, optionally, in apposition with a proximal tissue wall.

In various embodiments described or otherwise within the scope of the present disclosure, and in accordance with one aspect of the disclosure, once the tissue/organ has been manipulated (e.g., pulled back) to its desired location, the user may remove the tissue-manipulating device 110, or may continue the procedure either with the tissue-manipulating device 110 held in place, or with the tissue grasper assembly 120 deployed (separated from other components of the tissue-manipulating device 110 and left in place). For instance, the tissue grasper assembly 120 may be moved out of engagement with the treatment site TS, returned to a closed configuration, and moved proximally, such as out of the body. Further procedures may then be performed at the treatment site TS. Alternatively, the deployed tissue-manipulating device 110 may be left in place to maintain tissue in a desired location (such as in apposition with another tissue or organ), as the end or goal of the procedure, or may be used to close large tissue defects or perforations (e.g., within a single lumen). In some embodiments, the tissue grasper assembly 120 is formed with a collar or capsule or hypotube 126 (such terms being substantially interchangeable, the term "capsule" being used herein for the sake of convenience and without intent to limit) removably fitted on the distal end 115 of the shaft 116, with the grasper arms 122 coupled to or otherwise mounted in the capsule 126. In some embodiments, the capsule 126 is removable or separable from the shaft 116 to deploy the tissue grasper assembly 120 to remain at the treatment site TS (with the grasper arms 122 engaging the treatment site TS) and to remove the shaft 116 and the remaining elements of the tissue-manipulating device 110. It will be appreciated that references herein to a shaft or capsule may be interchangeable, a "capsule" not being limited to refer to a separate element coupled to a "shaft".

Figure 5A:
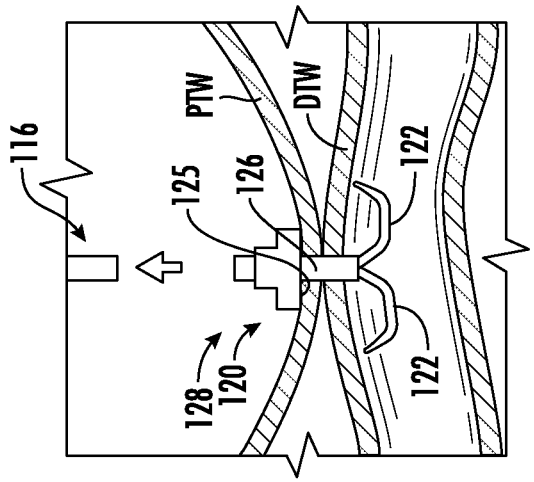
FIGS. 5A-5C illustrate an example of further positions of a tissue-manipulating device after reaching a position as illustrated in FIG. 4D.
Figure 5B:
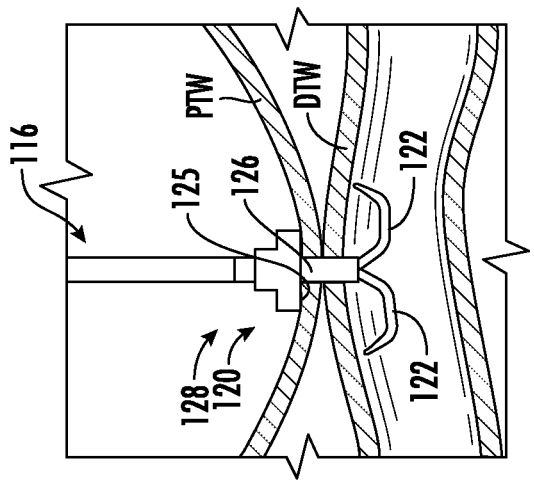
Figure 5C:
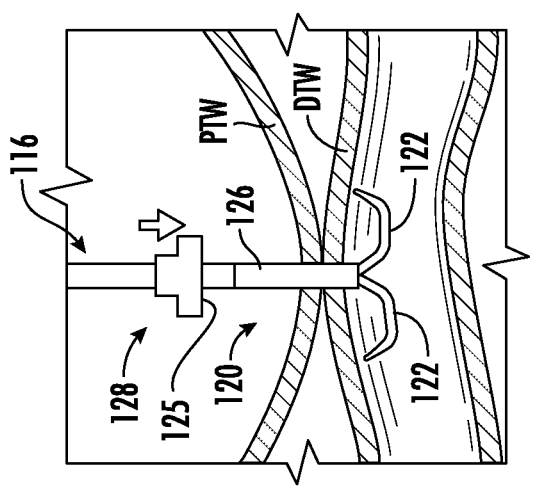

In one embodiment, illustrated in FIGS. 5A-5C, once a distal tissue wall DTW has been moved into apposition with a proximal tissue wall PTW (such as in accordance with the procedure or method illustrated in FIGS. 4A-4D), a locking feature 128, such as a collet or other suitable structure known or heretofore known in the art with elements shaped and configured to engage with an element of the tissue grasper assembly 120, may be actuated to hold the tissue grasper assembly 120 with the grasper arms 122 engaging tissue at the treatment site TS, such as in an open configuration, as illustrated in FIG. 5A. The locking feature 128 may engage the capsule 126 (or other component of the tissue grasper assembly 120) to hold the apposing tissues together, as illustrated in FIG. 5B. This may be accomplished with an outer catheter or an inner push rod or control wire responsible for holding and actuating the components in any of a variety of known manners. The locking feature 128 may include a flange or other region (e.g., widened region) providing a tissue-grasping surface 125 The shaft 116 may then be detached or decoupled from the tissue grasper assembly 120 (such as being detached or decoupled from the shaft 116) and proximally withdrawn from the treatment site TS, as illustrated in FIG. 5C. Frictional forces, locking tabs, barbs, positive stops, ratchet locks, etc., may be used or applied as known in the art. It will be appreciated that any of a variety of other locking features may be used in accordance with principles of the present disclosure to hold the tissue grasper assembly 120 and the grasper arms 122 in place once the shaft 116 has been decoupled therefrom.

Figure 6A:
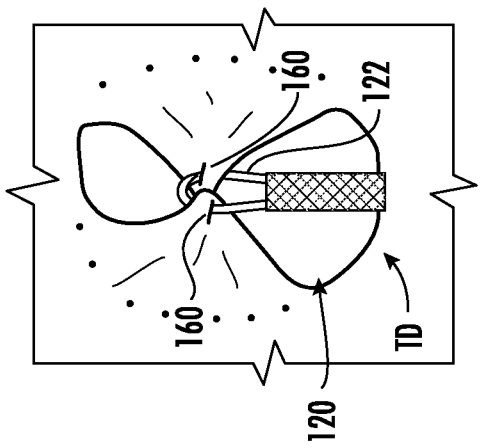
FIGS. 6A-6C illustrate sequential positions of a tissue-manipulating device formed in accordance with principles of the present disclosure with respect to a tissue defect to be repaired in accordance with principles of the present disclosure.
Figure 6B:
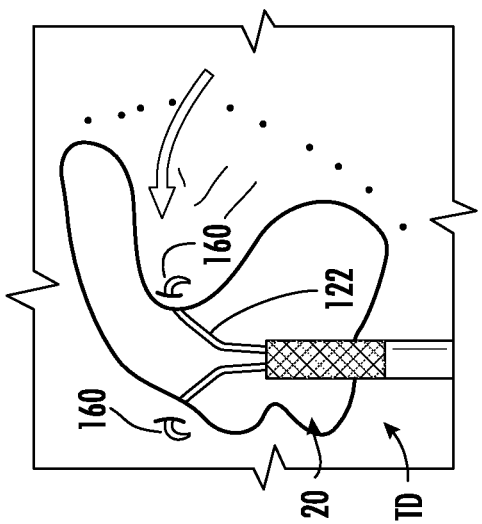
Figure 6C:
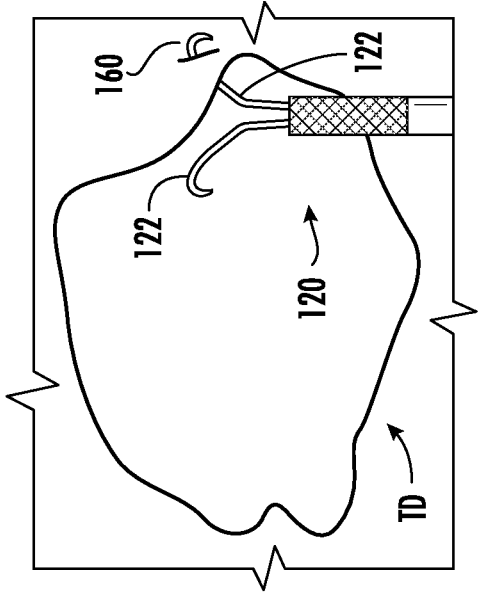

As may be appreciated, and as mentioned above, a tissue-manipulating device 110 in accordance with principles of the present disclosure may be used in a variety of procedures other than drawing and/or holding together tissue walls of different organs or lumens. For example, as illustrated in FIGS. 6A-6C, a tissue-manipulating device 110 may be used to repair a defect, such as by drawing together tissue walls at different (e.g., opposite) sides or edges of the defect. As illustrated in FIG. 6A, a tissue grasper assembly 120 may be advanced to a tissue defect TD and one of the grasper arms 122 may be engaged with tissue wall along a side or edge of the tissue defect TD, such as by engaging a grasping feature 160 of the grasper arm 122 with the tissue. The tissue grasper assembly 120, with the grasper arms 122 in an open configuration, along with the grasped tissue, is then moved across the defect and another grasper arm 122 is engaged with another region of the tissue wall along the tissue defect TD (such as tissue wall on an opposite site of the tissue defect from the already-grasped tissue wall section), as illustrated in FIG. 6B. A grasping feature 160 on the grasper arm 122 engaging the initially-grasped tissue region may facilitate maintaining the hold of the grasper arm 122 on the initially-grasped tissue region. With different regions of tissue along the tissue defect TD engaged by different grasper arms 122, the tissue grasper assembly 120 is moved into a closed configuration, as illustrated in FIG. 6C, to pull or draw the tissue together. A locking feature 128, for example as illustrated in FIGS. 5A-5C, may be used to maintain the relative positions and grasping of the tissue grasper assembly 120 and the grasped tissue region. The tissue grasper assembly 120 may be left in place in the closed configuration, holding the tissue walls in apposition and decreasing the size of the tissue defect TD to allow for the defect to heal. As may be appreciated, the grasping feature 160 may facilitate the holding of the tissue grasper assembly 120 onto the tissue during the entire repair procedure.

As will be appreciated, various alternative configurations of tissue grasper assemblies 120 which are expandable from a closed configuration to an open configuration are within the scope of the present disclosure, as will now be described. For example, various tissue grasper assemblies within the scope of the present disclosure, such as illustrated in FIGS. 7A-7C, 8A-8C, 9A-9C, and 10A-10C, are formed with grasper arms which are resilient and biased to extend into or be held in an open configuration. Other tissue grasper assemblies are expandable from a closed configuration to an open configuration, such as illustrated in FIGS. 11A, 11B, 12A, and 12B.

As briefly described above, a sharpened element may be provided at the distal end of a tissue-manipulating device formed in accordance with various principles of the present disclosure, such as shown in the example of a tissue grasper assembly 420 illustrated in FIGS. 7A-7C. The sharpened element 450 may be formed at a distal end 421 of the grasper arms 422 to extend distally therefrom. The sharpened element 450 may encounter tissue wall at a treatment site TS and puncture the tissue wall to allow the remainder of the tissue grasper assembly 420 to extend therethrough. The grasper arms 422 of the tissue grasper assembly 420 of FIGS. 7A-7C and other features of the tissue grasper assembly 420 may be otherwise substantially similar to the features of the tissue grasper assembly 220 illustrated in FIGS. 2A-2C.

A different configuration of resiliently biased grasper arms is illustrated in FIGS. 8A-8C. The grasper arms 522 of the tissue grasper assembly 520 of FIGS. 8A-8C may be configured as two or more (such as three or four or more) curved bars housed inside a shaft 516 (or a removable capsule 526 coupled to the shaft, such as the removable capsules described above) and biased into a stored configuration extending along the longitudinal axis LA of the shaft 516 or capsule 526 and/or tissue grasper assembly 520. Upon actuation of a tissue-manipulating device controller (such as illustrated in the embodiments of FIG. 2A-2C or 7A-7C), the grasper arms 522 may be advanced distally to extend distally from the shaft 516 or the capsule 526. The grasper arms 522, no longer confined within and constrained by the shaft 516 or capsule 526, are free to expand or extend outwardly (e.g., radially outwardly or transverse) with respect to the longitudinal axis LA, as illustrated in FIG. 8C. At least two of the grasper arms 522 extend in different directions when in the open configuration to present a grasper surface 525 configured and shaped and with sufficient surface area to engage with tissue to be manipulated. A tissue grasping feature 560, such as a barb or hook or jaws or other tissue-engaging projection, may be provided to facilitate grasping of tissue, as described above with reference to earlier-described embodiments.

In another embodiment formed in accordance with principles of the present disclosure, and illustrated in FIGS. 9A-9C, a tissue grasper assembly 620 is formed with substantially straight grasper arms 622 such as in the form of resilient elongated elements or bars. As a tissue-manipulating device controller 630 (such as any of the tissue-manipulating device controllers described herein) is manipulated to advance the tissue grasper assembly 620 distally, the grasper arms 622 extend from the distal end 615 of the shaft 616 (or a removable capsule 626 coupled to the shaft, such as the capsules described above). As the grasper arms 622 exit the distal end 615 of the shaft 616 or capsule 626, the grasper arms 622 encounter a diverting feature 627 (such as a wall or other obstacle or obstruction) at the distal end 615 of the shaft 616 or capsule 626 and are bent or deflected to exit transverse to the longitudinal axis LA of the tissue grasper assembly 620, through respective exit openings 629, such as to form a "T" shape when opened, as illustrated in FIGS. 9B and 9C, presenting a grasper surface 625 proximally for engagement with a tissue wall. A tissue grasping feature 660, such as a hook or barb or other tissue-engaging projection, may be provided or formed at one or more of the free ends 621 of the grasper arms 622 to facilitate grasping of tissue.

It will be appreciated, such as with reference to the embodiment illustrated in FIGS. 10A-10C, that a tissue grasper assembly may be formed with a single grasper arm similar to the grasper arms of the embodiment of FIGS. 9A-9C. More particularly, with reference to the tissue grasper assembly 720 illustrated in FIGS. 10A-10C, a single elongated grasper arm 722 may be held or confined within a shaft 716 (or a removable capsule 726 coupled to the shaft, such as the capsules described above) and biased into a stored configuration extending along the longitudinal axis LA of the shaft 716 or capsule 726 and/or tissue grasper assembly 720. As with the tissue grasper assembly 620 of FIGS. 9A-9C, as a tissue-manipulating device controller 730 (such as any of the tissue-manipulating device controllers described herein) is manipulated to advance the tissue grasper assembly 720 distally, the grasper arm 722 extends from the distal end 715 of the shaft 716 (or a removable capsule 726 coupled to the shaft, such as the capsules described above). As the grasper arm 722 exits the distal end 715 of the shaft 716 or capsule 726, the grasper arm 722 encounters a diverting feature 727 (such as a wall or other obstacle or obstruction) at the distal end 715 of the shaft 716 or capsule 726, and is bent or deflected to exit transverse to the longitudinal axis LA of the tissue grasper assembly 720, as illustrated in FIG. 10C. In contrast with the diverting feature 627 of the tissue grasper assembly 620 of FIGS. 9A-9C, the diverting feature 727 of the tissue grasper assembly 720 of FIGS. 10A-10C preferably has a single exit opening 729 to direct the grasper arm 722 in the desired direction. A tissue grasping feature 760, such as a hook or barb or other tissue-engaging projection, may be provided or formed along the grasper arm 722 to facilitate grasping of tissue. More than one tissue grasping feature 760 is illustrated, such as one at the free end 721 of the grasper arm 722 and additional tissue grasping features 760 extending along the grasper surface 725 of the grasper arm 722. However, it will be appreciated that the tissue grasping feature 760 may be in other configurations such as described herein.

A grasper arm of a tissue grasper assembly of a tissue-manipulating device formed in accordance with various principles of the present disclosure may be resiliently biased to expand away from the shaft of the tissue-manipulating device in a direction in addition to radially outward. For instance, as illustrated in the embodiment of FIGS. 11A and 11B, a tissue-manipulating device 810 may have a tissue grasper assembly 820 with a spiral-shaped grasper arm 822 held in a substantially compact or elongated/straight configuration within the shaft 816 of the tissue-manipulating device 810 (or a removable capsule 826 coupled to the shaft, such as the capsules described above, or within the delivery device of the tissue-manipulating system 100) in a closed configuration, as illustrated in FIG. 11A. The grasper arms 822 may be actuated to move between a closed configuration and an open configuration such as upon actuation of a tissue-manipulating device controller, not shown but which may be configured as described with respect to other embodiments described herein. The grasper arms 822 may be coupled to the tissue grasper assembly 820 in any manner known or heretofore in the art, such as via a controller coupling as described herein with reference to other embodiments. In one embodiment, distal movement of the grasper arm 822 causes the distal end 821 to extend from the distal end 815 of the shaft 816 or capsule 826, such as through an exit opening 829. When no longer constrained by the shaft 818, the grasper arm 822 may expand into a spiral shape configured and dimensioned (with a greater outer diameter than the outer diameter of the shaft 816 or capsule 826, and with sufficient volume) to engage tissue such that movement or manipulation of the tissue-manipulating device 810 to move or manipulate the tissue grasper assembly 820 causes the desired manipulation of the engaged tissue. For instance, in one embodiment the spiral configuration includes more than one turn of the grasper arms 322, the turns of the spiral being substantially concentric and coplanar to form a grasper surface 825 comprising the multiple turns of the spiral. It will be appreciated that other configurations extending sufficiently radially outward to engage tissue and having sufficient strength to pull the tissue as the tissue grasper assembly 820 is moved proximally is within the scope of the present disclosure.

A grasper arm of a tissue grasper assembly of a tissue-manipulating device formed in accordance with various principles of the present disclosure may be otherwise expandable to expand away from the shaft of the tissue-manipulating device. For instance, as illustrated in the embodiment of FIGS. 12A and 12B, a tissue-manipulating device 910 may have a tissue grasper assembly 920 with a grasper arm 922 in the form of a radially-outwardly expandable element such as a balloon. The grasper arm 922 is held in a substantially compact configuration within the shaft 916 of the tissue-manipulating device 910 in a closed configuration, as illustrated in FIG. 12A. The grasper arm may extended distally out of the shaft 916 to be expanded, such as inflated, in accordance with various known or heretofore know methods used to expand such grasper arm. The grasper arm 922 may be moved into engagement with tissue such that movement or manipulation of the tissue-manipulating device 910 to move or manipulate the tissue grasper assembly 920 causes the grasper arm 922 to move or manipulate the engaged tissue. A sharpened element 950, such as a sharp tip or needle, may be provided at the distal end 915 of the shaft 916 so that the tissue grasper assembly 920 may puncture the tissue wall through which the tissue grasper assembly 920 it is to extend.

In accordance with one aspect of the present disclosure, a resiliently biased grasper arm may be in the form of a wire, such as a wire resiliently biased into a tissue-hooking configuration. Generally speaking, with reference to FIGS. 13A and 13B, a tissue-manipulating device 1110 may have a tissue grasper assembly 1120 with a grasper arm 1122 in the form of a wire with a distal end 1121 bent into the form of a barb or hook (such terms being used interchangeably herein without intent to limit). The tissue grasper assembly 1120 may be distally advanced through a preformed opening in the tissue (or may puncture the tissue) at the treatment site TS and the hooked distal end 1121 of the grasper arm 1122 is moved into engagement with a distal surface of the tissue. The bent distal end 1121 of the grasper arms 1122 may be made of a shape-memory alloy (such as Nitinol) to facilitate the distal end 1121 passing through the working channel of the shaft 1116 or other delivery device in a straight configuration, before reforming into a hook upon exiting the distal end of the shaft 1116 or delivery device, such as upon reaching the treatment site TS. In some embodiments, such as described herein, the tissue grasper assembly 1120 is extended through a proximal tissue wall PTW and a distal tissue wall DTW, and the tissue grasper assembly 1120 is moved proximally to draw the walls together, such as into apposition. The distal end 1121 of the grasper arm 1122 may be sufficiently sharp to pierce the proximal tissue wall PTW. Once the tissues are positioned as desired, such as via a controller (such as a controller as disclosed herein with reference to other embodiments, or another suitable controller known or heretofore known in the art), a locking feature 1128 may be deployed to hold the grasper arm 1122 in position relative to the tissue(s). In one embodiment, the locking feature 1128 includes a retaining feature 1170, such as a deployment cap or deploy collar or deploy capsule, having a grasper surface 1175 configured to engage a proximal surface of the proximal tissue wall PTW and, in conjunction with the grasper arm 1122, hold the proximal tissue wall PTW and the distal tissue wall DTW in position. In one embodiment, the retaining feature 1170 may be configured to retain the distal end 1121 of the grasper arm 1122 in place. The retaining feature 1170 may also encase or shield or bury an optionally sharpened tip or distal end 1121 of the grasper arm 1122 to protect surrounding tissue against possible trauma. A proximal region of the wire forming the grasper arm 1122 may be broken, such as, without limitation, by a tension ball method (e.g., ball in cup configuration, separating upon proximal pulling of the wire away from the treatment site TS), breaking the wire along a pre-weakened area, uncrimping a capsule, or deforming/breaking tabs, or other structure breaking upon further tensile loading on the wire.

Figure 13A:
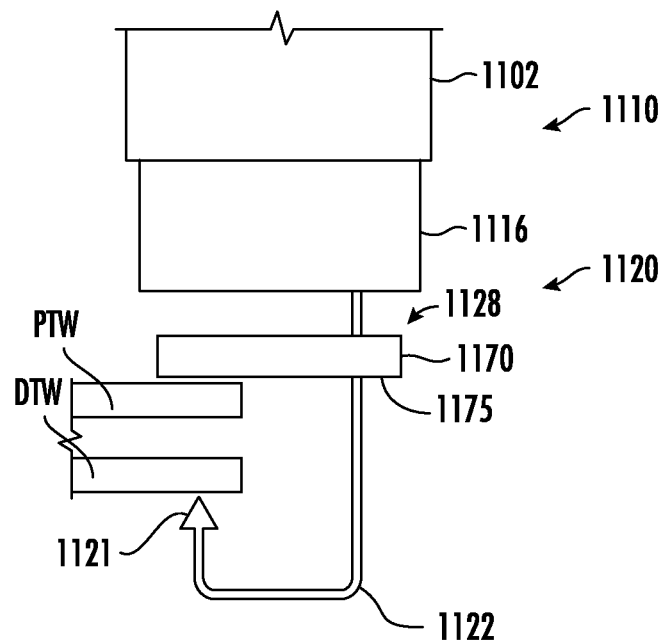
FIG. 13A is an elevational view of a tissue-manipulating device formed in accordance with principles of the present disclosure with respect to tissues to be drawn together in accordance with principles of the present disclosure.
Figure 13B:
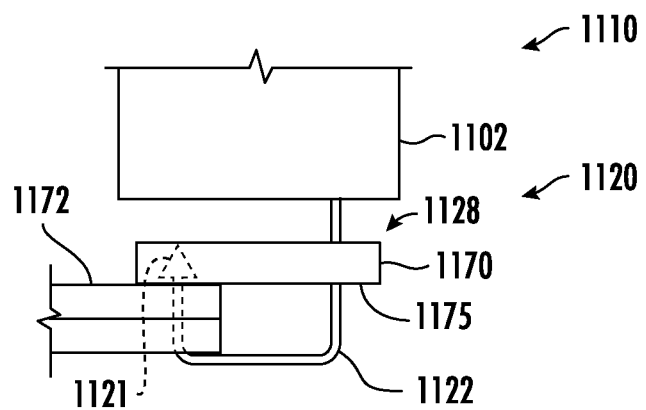
FIG. 13B is an elevational view of a tissue-manipulating device as in FIG. 13A drawing together tissue walls.
Figure 14:
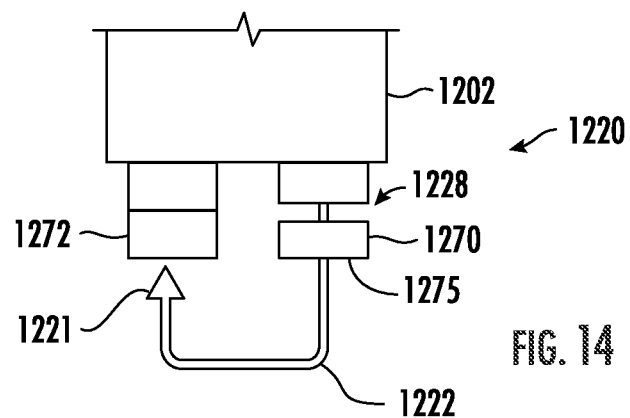
FIG. 14 is an elevational view of a tissue-manipulating device formed in accordance with principles of the present disclosure.

In one embodiment, such as illustrated in FIG. 14, a tissue-manipulating device 1210 similar to a tissue-manipulating device 1110 as illustrated in FIGS. 13A and 13B may utilize delivery device 1202 with more than one lumen, such as a dual-lumen endoscope. The grasper arm 1222, such as in the form of a wire with a preformed barb or hook at its distal end, may be distally advanced through a working channel of a first lumen. The hook may be shaped such that the distal end 1221 of the grasper arms 1222 (e.g., the barb tip) can be aligned with another working channel of the delivery device 1202. Once the tissues are positioned as desired, such as via a controller (such as a controller as disclosed herein with reference to other embodiments, or another suitable controller known or heretofore known in the art), a locking feature 1228 may be deployed to hold the grasper arm 1222 in position relative to the tissue(s), and held, for instance, by a friction fit. In one embodiment, the locking feature 1228 includes a retaining feature 1270, such as in the form of a collar or disk (such terms being used for the sake of simplicity, and used interchangeably herein without intent to limit, and are not intended to limit such element to a circular cross-sectional shape or otherwise), having a grasper surface 1275 configured to engage a proximal surface of the tissue at the treatment site, and, in conjunction with the grasper arm 1222, to hold the tissue at the treatment site in the desired position. The retaining feature 1270 may serve as a deployment feature and/or as a stop to hold tissue in place post-deployment.

Figure 15:
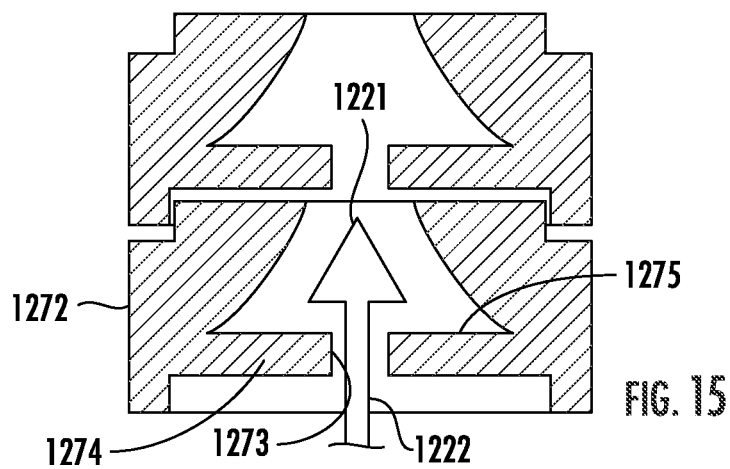
FIG. 15 is a cross-sectional view through locking caps which may be used with a tissue-manipulating device as in FIG. 14.

The locking feature 1228 may additionally include a deploy collar 1272, such as a protective cap. In some embodiments, the deploy collar 1272 is deployed through or otherwise positioned at another working channel of the delivery device 1202 (e.g., the working channel with which the distal end 1221 of the grasper arm 1222 is aligned once advanced out of the first working channel of the delivery device 1202). The deploy collar 1272 may be sized and shaped to receive the optionally sharpened tip of the distal end 1221 of the grasper arm 1222, such as after it has pierced the tissue in the desired location. The deploy collar 1272 may serve to stop or to hold the tissue and/or to encase or shield or bury a sharp tip (if provided) at the distal end 1221 of the grasper arm 1222 to protect surrounding tissue against possible trauma. An example of an embodiment of a tubular deploy collar 1272 is shown in cross-section in FIG. 15, illustrating a through hole 1273 within the deploy collar 1272 through which the distal end 1221 of the grasper arm 1222 may pass. The through hole 1273 may be formed in a retaining wall 1274 extending radially inwardly from an inner wall of the collar. The distal end 1221 of the grasper arm 1222 may be resiliently biased outwardly, and compressed to pass through the retaining wall 1274. The retaining wall 1274 may provide a retaining surface 1275 at a proximal side of the retaining wall 1274 such that once the distal end 1221 of the grasper arm 1222 passes through the through hole 1273, the distal end 1221 expands to its relaxed expanded configuration (wider in a direction transverse to the remaining proximally extending portion of the wire than the diameter of the through hole 1273) and is prevented from being retracted distally through the through hole 1273, and thereby is locked into position with respect to the deploy collar 1272 and the treatment site. As may be appreciated, multiple retaining features 1270 and/or multiple deploy collars 1272 may be provided on the tissue grasper assembly 1220, and may be coupled together such as via a light press-fit or similar feature. It will also be appreciated that a tissue-manipulating device 1210 as illustrated in FIG. 14 may be supplied with one or more grasper arms 1222, with one or more of which including metal barb devices or the like.

Figure 16:
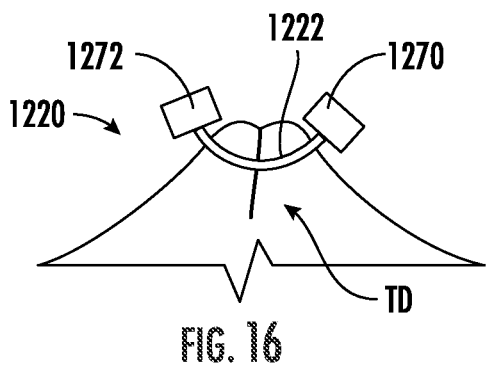
FIG. 16 illustrates a tissue-manipulating device as in FIG. 15 in position repairing a tissue defect.
Figure 17:
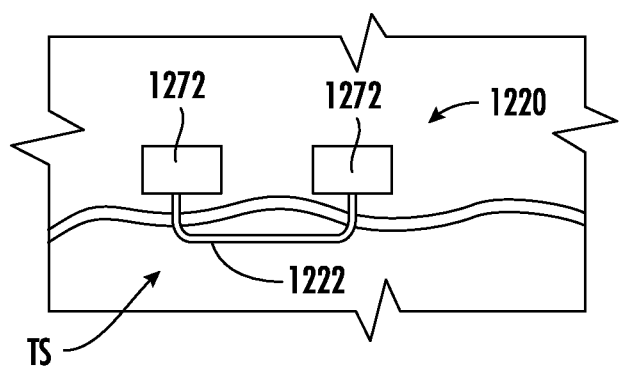
FIG. 17 illustrates a tissue-manipulating device as in FIG. 15 in position holding tissues in apposition.

Referring to FIG. 16 and FIG. 17, the tissue-manipulating device 1210 of FIG. 14 may be used to close defects or to pull and hold two separate lumens together. For instance, as illustrated in FIG. 16, tissue at different sides of a tissue defect TD may be drawn together by the grasper arm 1222 and the tissue grasper assembly 1220 held in place by retaining or locking a retaining feature 1270 at one side of the tissue defect TD and a deploy collar 1272 at the other side of the tissue defect TD. As illustrated in FIG. 17, the grasper arm 1222 may be looped through tissue to be held together in apposition at a treatment site TS. The tissue grasper assembly 1220 is held in place by retaining or locking a retaining feature 1270 at the entry site (at which the tissue grasper assembly 1220 initially enters the treatment site TS, and where the proximal end of the tissue grasper assembly 1220 is located once the tissue grasper assembly 1220 has been deployed at the treatment site TS) and by retaining or locking a deploy collar 1272 at the exit site (at which the distal end 1201 of the tissue grasper assembly 1220 exits the treatment site TS, and where the distal end of the tissue grasper assembly 1220 is located once the tissue grasper assembly 1220 has been deployed at the treatment site TS).

Figure 18:
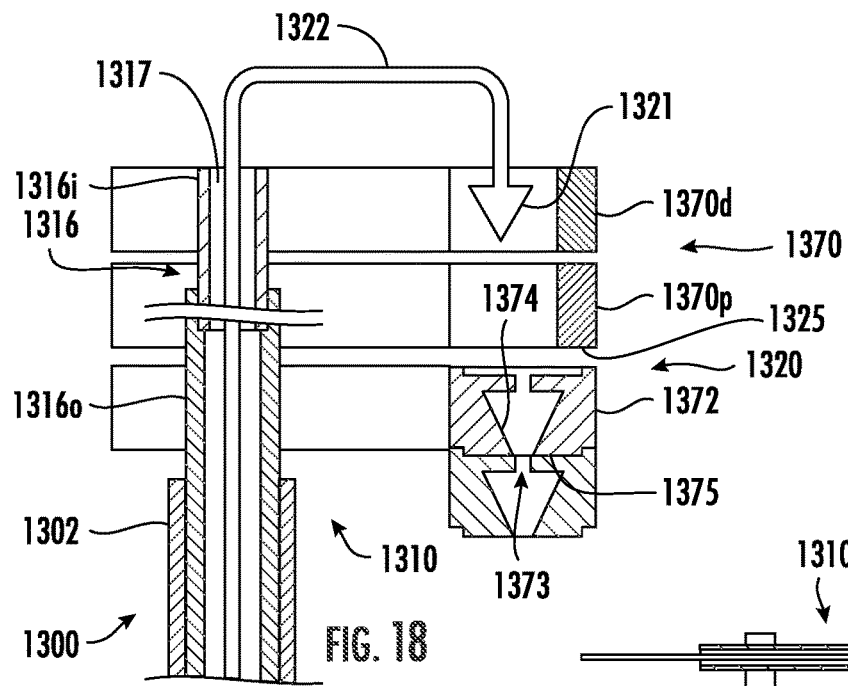
FIG. 18 is a cross-sectional view of a tissue-manipulating device formed in accordance with principles of the present disclosure.

In some embodiments, a grasper arm in the form of a resiliently biased wire may be used in a tissue-manipulating device suitable for closing large defects, such as in the example of a tissue-manipulating device 1310 illustrated in FIG. 18. As in the tissue-manipulating device 1210 illustrated in FIG. 14, the tissue-manipulating device 1310 includes a grasper arm 1322, such as in the form of a wire with a preformed barb or hook at its distal end. The hook may be shaped such that the distal end 1321 of the grasper arms 1322 (e.g., the barb tip) is proximally-facing. The grasper arm 1322 may extend through a lumen 1317 defined through a shaft 1316. The shaft 1316 may be distally advanced through a working channel of a delivery device 1302, such as of a tissue-manipulating system 1300, to advance the tissue-manipulating device 1310 to the treatment site. Alternatively, the shaft 1316 may be delivered in an over-the-scope delivery, including alongside (optionally without fully surrounding) the scope.

The tissue grasper assembly 1320 of the tissue-manipulating device 1310 of FIG. 18 may include one or more tissue retaining features 1370 which may be carried by the shaft 1316 and associated with the grasper arm 1322, such as by the grasper arm 1322 passing through a portion of the tissue retaining feature 1370. The tissue retaining features 1370 may be in the form of a grasping collar or disk (such terms being used for the sake of simplicity, and used interchangeably herein without intent to limit, and are not intended to limit such element to a circular cross-sectional shape or otherwise) with a grasper surface 1325 configured to engage a proximal surface of the tissue at the treatment site, and, in conjunction with the grasper arm 1322, to hold the tissue at the treatment site in the desired position. The grasper arm 1322 and retaining feature 1370 may be movable with respect to one another, such as independently of one another, to allow the various elements to engage tissue at a treatment site to manipulate the tissue to effect the desired procedure or otherwise on the tissue. In one embodiment, the shaft 1316 has an inner shaft 1316*i* carrying a distal retaining feature 1370*d* and an outer shaft 1316*o* carrying a proximal retaining feature 1370*p* to allow for relative movement between the retaining features 1370 to grasp or manipulate tissue and/or to retain tissue therebetween.

A deploy collar 1372 may be movably carried by the shaft 1316 or separately deployed to hold the tissue grasper assembly 1320, including the grasper arm 1322 and the one or more retaining features 1370, in place as desired at a treatment site. As in the deploy collar 1272 illustrated in FIG. 15, the grasper arm 1322 of the tissue grasper assembly 1320 of the tissue-manipulating device 1310 of FIG. 18 may be held (e.g., restrained or locked) with respect to the deploy collar 1372 such as by engaging a retaining wall 1374 extending radially inwardly from an inner wall of the deploy collar 1372. More specifically, the distal end 1321 of the grasper arm 1322 may be resiliently biased outwardly, and may be compressed to pass through a through hole 1373 in the retaining wall 1374. The retaining wall 1374 may provide a retaining surface 1375 at a proximal side thereof such that once the distal end 1321 of the grasper arm 1322 passes through the through hole 1373, the distal end 1321 expands to its relaxed expanded configuration (wider in a direction transverse to the remaining proximally extending portion of the wire than the diameter of the through hole 1373) and is prevented from being retracted through the through hole 1373 and thereby is locked into position with respect to the deploy collar 1372 and the treatment site. More than one deploy collar 1372 may be provided, with the more than one deploy collars 1372 being coupled together such as with a light press-fit or similar feature. If desired, a distal deploy collar 1372 may be carried by the shaft 1316 and more proximal deploy collars 1372 may be deployed separately, such as through another working channel of the delivery device 1302.

Figure 19A:
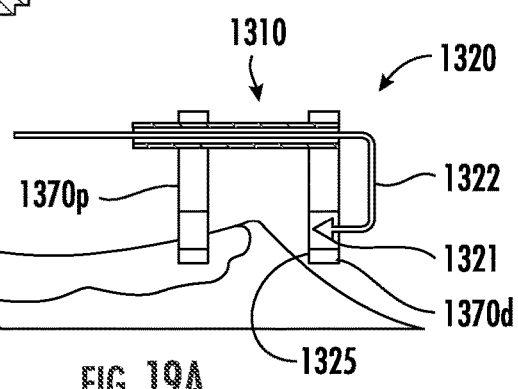
FIGS. 19A-19E illustrate sequential positions of a tissue-manipulating device as in FIG. 18 with respect to a tissue defect to be repaired in accordance with principles of the present disclosure.
Figure 19B:
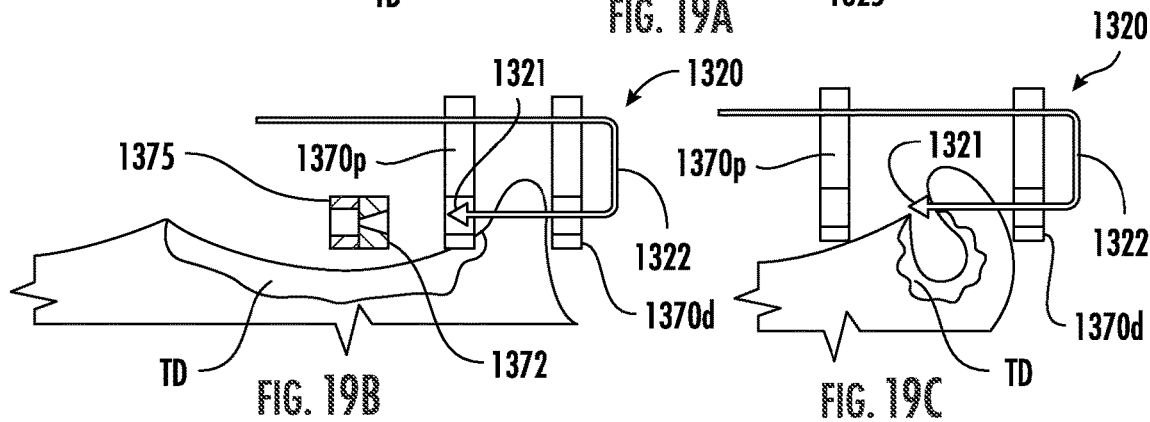
Figure 19C:
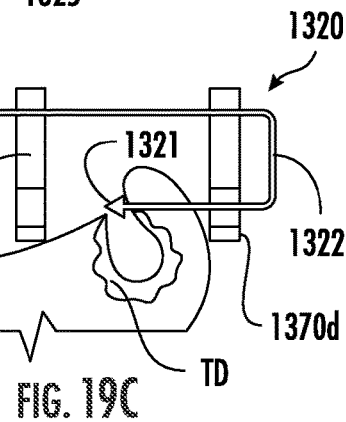
Figure 19D:
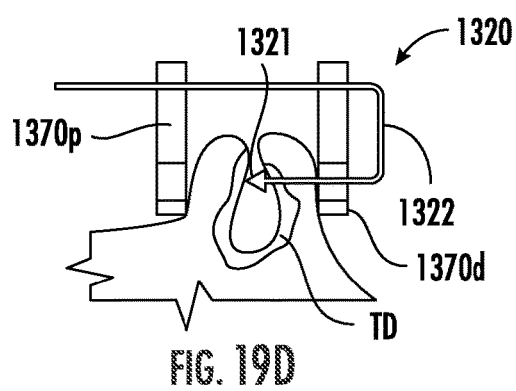
Figure 19E:
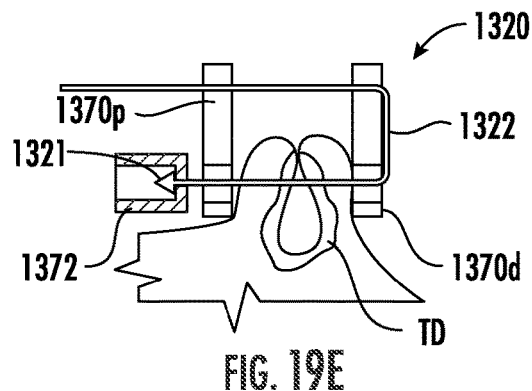

The tissue-manipulating device 1310 of FIG. 18 may be used to close defects, such as illustrated, for example, in FIGS. 19A-19E. For instance, as illustrated in FIG. 19A, the distal retaining feature 1370*d* may be positioned distal to a distal tissue region alongside a tissue defect TD to engage the distal tissue. The proximal retaining feature 1370*p* may be positioned at a proximal side of the engaged distal tissue. The distal retaining feature 1370*d* may be moved proximally toward the proximal retaining feature 1370*p* to draw together the retaining features 1370*d*, 1370*p* to grasp the initially-engaged distal tissue therebetween, as illustrated in FIG. 19B, such as by maintaining the distal retaining feature 1370*d* and the proximal retaining feature 1370*p* in proximity (e.g., by controlling the relative positions of the inner shaft 1318*i* and the outer shaft 1316*o* respectively carrying the distal retaining feature 1370*d* and the proximal retaining feature 1370*p*). The distal end 1301 of the grasper arm 1322 (facing proximally) may be provided with a sharpened tip to pierce the pinched tissue and pass therethrough. The grasped distal tissue may be manipulated or drawn or pulled proximally to proximal tissue on another side of the tissue defect TD, as shown in FIG. 19C. The proximal retaining feature 1370*p* is moved proximally away from the distal retaining feature 1370, as also illustrated in FIG. 19C, to allow proximal tissue on another side of the tissue defect TD to be positioned between the tissue retaining features 1370*d*, 1370*p* to be grasped therebetween, as illustrated in FIG. 19D, such as to hold the tissue regions on different sides of the defect together to repair or to close the defect. The distal end 1301 of the grasper arm 1322 may be further moved proximally so that the sharpened tip thereof pierces the proximal tissue. The deploy collar 1372 is then moved into position and the distal end 1301 of the grasper arm 1322 may be held therein, retaining the grasped tissue regions together to repair the defect. As illustrated in FIG. 19E, the deploy collar 1372 may be configured to take the place of the proximal retaining feature 1370*p* (which may be removed and retrieved) at a position proximal to the repaired defect. As may be appreciated, the deploy collar 1372 may encase or shield or bury the sharp tip of the grasper arms 1322 therein to protect surrounding tissue against possible trauma. The distal retaining feature 1370*d* deploys with the tissue grasper assembly 1320, holding the tissue in place. The proximal retaining feature 1370*p* may deploy with the tissue grasper assembly 1320 or may remain attached to the shaft 1316. The grasper arm 1322 may fracture or otherwise disconnect from a proximal portion of the tissue-manipulating device 1310 for deployment. For instance, the grasper arm 1322 may be held by protrusions or locking tabs or the like, or with a friction fit within the inner shaft 1316*i*, which may disconnect from the outer shaft 1316*o* upon deployment and remain with the deployed components of the tissue grasper assembly 1320. The deployed portion of the barb at the distal end 1301 of the grasper arm 1322 may contain an additional node or collar or further barbs that catch on the deploy collar 1372 to aid in keeping the defect closed following deployment. Although FIGS. 19A-19E may be understood as illustrating use of a tissue-manipulating device 1310 to close defects, such as within a lumen of the gastrointestinal (GI) tract, the illustrated tissue-manipulating device 1310 may additionally or alternatively be used to pull the intestines to the stomach for other GI procedures, such as gastric bypass procedures. Several tissue grasper assemblies 1320 may be deployed around the newly created orifice, potentially forming a permanent fistula.

It will be appreciated in view of the above, the tissue-manipulating device 1310 of FIGS. 18 and 19A-19E may be small enough to fit within the working channel of a delivery device such as an endoscope, or may be an over-the-scope device, or a hybrid device that features one or both retaining features 1370*d*, 1370*p* over-the-scope and the deploy collar 1372 through-the-scope, and the grasper arm 1322 either over-the-scope or through-the-scope. In some embodiments, such as in the case of a hybrid device, the proximal retaining feature 1370*p* could be replaced by a endoscopic cap, such as those commonly used for endoscopic submucosal dissection (ESD) and endoscopic submucosal resection (EMR) procedures. A hybrid device could also allow for multiple grasper arms 1322 to be used with a single pair of retaining features 1370.

In accordance with various principles of the present disclosure, yet a further tissue-manipulating device may be formed utilizing principles of resiliently biased grasper arms such as described broadly herein. An embodiment of a tissue-manipulating device 1410 configured to pull together tissue walls into apposition is illustrated in FIGS. 20A-20C. The tissue-manipulating device 1410 may be configured to be left in place anchoring together tissue walls (e.g., a portion of the intestines being anchored to the stomach such as for a gastric bypass procedure) and may thus be characterized as a rivet. As illustrated, the tissue-manipulating device 1410 has one or more grasper arms 1422, such as in the form of curved bars, with a collar or capsule 1426 around the middle of the tissue-manipulating device 1410 between proximal grasper arms 1422*p* and distal grasper arms 1422. The tissue grasper assembly 1420 (capsule 1426 and grasper arms 1422) may be loaded into another sleeve, such as a delivery device, e.g., a flexible elongate member 102, of the tissue-manipulating system 100, or the shaft 1416 of the tissue-manipulating device 1410, as shown in FIG. 20A. The flexible elongate member 102 or shaft 1416 biases the grasper arms 1422 into a closed extended configuration, substantially flattened and extending along the longitudinal axis LA of the capsule 1426 or tissue grasper assembly 1420 or shaft 1416, such that the device can be passed through the working channel of the shaft 1416 and/or flexible elongate member 102 of the tissue-manipulating system 100. The friction from the resiliently biased grasper arms 1422 (normally biased to extend into a radially-outwardly extending open configuration, as illustrated in FIG. 20C) on the inside of the shaft 1416 might be sufficient to keep the tissue grasper assembly 1420 in place within the shaft 1416, but, if not, an internal connection to the grasper arms 1422 and/or capsule 1426 might be required. Any connection or elements known or heretofore known in the art allowing for detachment for deployment as desired may be used, such as detachable push rods used in hemostatic clipping and allowing for detachment.

As illustrated in FIG. 20A, the distal end 1411 of the tissue-manipulating device 1410 is passed through openings (e.g., preformed) in the tissue walls to be drawn together, until the distal end 1415 of the shaft 1416 is positioned past the distal tissue wall DTW to place the distal end of the tissue grasper assembly 1420 within the distal lumen. In the illustrated example, the distal end 1415 of the shaft 1416 is passed through an opening in the target intestine wall. The capsule 1426 along with the distal grasper arms 1422*d* are partially pushed distally out of the distal end 1415 of the sleeve 1416, as shown in FIG. 20B, to allow the distal grasper arms 1422*d* to expand radially outwardly. The distal tissue wall DTW (e.g., intestine) may now be dragged back to the opening created in the proximal tissue wall PTW (e.g., stomach wall). Next, the shaft 1416 is further proximally retracted, allowing the proximal grasper arms 1422*p* be released from the shaft 1416 and to expand radially outwardly into the open configuration shown in FIG. 20C. If an internal connection to tissue grasper assembly 1420 was required, it may now be severed to completely deploy the tissue grasper assembly 1420 to anchor together the distal tissue wall DTW and the proximal tissue wall PTW.

In view of the above descriptions, it will be appreciated that the devices, systems, and methods disclosed herein can be used to form one or more anastomoses, and can be used with basic endoscopic tools, catheters, laparoscopes, general surgery tools, etc. For example, a catheter-based stent delivery device can be used with an endoscope to form one anastomosis, for example between two portions of the intestines. An endoscopic-based device could be used to form an anastomosis between the fundal pouch and a portion of the intestines, such as the jejunum. A combination of a laparoscopic-based device and a catheter-device as described herein could also be used to form a single anastomosis.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure. Reference signs in the claims are provided merely as a clarifying example and shall not be construed as limiting the scope of the claims in any way.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "the", "first", "second", etc., do not preclude a plurality. Reference signs in the claims are provided merely as a clarifying example and shall not be construed as limiting the scope of the claims in any way.

What is claimed is:

1. A tissue manipulating device comprising:
   a shaft extending along a longitudinal axis and having a proximal end and a distal end;
   a tissue grasper assembly extending along the distal end of said shaft and comprising one or more resilient grasper arms expandable between a closed configuration extending along the longitudinal axis of said shaft, and an open configuration outside said shaft and with said one or more grasper arms extending transversely away from the longitudinal axis of said shaft;
   a grasper surface, associated with at least one of said grasper arms, shaped and configured to engage a body tissue; and
   a controller coupled to said tissue grasper assembly via a controller coupling and configured to move said grasper arms between the closed configuration and the open configuration;
   wherein:
   in the closed configuration of said one or more grasper arms, said one or more grasper arms are positioned to present an atraumatic convex surface to body tissue; and
   in the open configuration of said one or more grasper arms, said grasper surface of said at least one grasper arm is directed toward the proximal end of said shaft to engage body tissue.

2. The tissue manipulating device of claim 1, wherein said grasper arms are resiliently biased in an open configuration in a radially outward direction away from said shaft when moved from a position within said shaft to a position outside said shaft.

3. The tissue-manipulating device of claim 1, wherein said grasper arms are resiliently held in an open configuration by a diverting feature formed on a distal end of said shaft.

4. The tissue manipulating device of claim 1, wherein said tissue grasper assembly is separable from said shaft and said controller to remain deployed grasping body tissue.

5. The tissue-manipulating device of claim 4, wherein said tissue grasper assembly comprises a locking feature engageable to hold said at least one grasper arm engaging tissue when said tissue grasper assembly is separated from said shaft and said controller.

6. The tissue-manipulating device of claim 4, further comprising a controller coupling coupled between said grasper arms and said controller, and movable upon actuation of said controller to move said at least one grasper arm between the closed configuration and the open configuration, said controller being separable from said controller coupling to deploy said tissue grasper assembly.

7. The tissue manipulating device of claim 4, wherein said tissue grasper assembly further comprises a capsule coupled to said shaft, said grasper arms being coupled to said shaft via said capsule, said tissue grasper assembly being separable with said capsule from said shaft and said controller to remain deployed grasping body tissue.

8. The tissue-manipulating device of claim 1, wherein at least one of said grasper arms includes a tissue grasping feature facing proximally toward said shaft when said grasper arms are extended distally outside said shaft and expanded into the open configuration.

9. The tissue-manipulating device of claim 1, further comprising a sharpened element extending distally from a distal end of said tissue grasper assembly and configured for puncturing a body tissue wall.

10. The tissue-manipulating device of claim 1, wherein said at least one grasper arms is a resiliently biased wire and said grasper surface is a provided on a tissue retaining feature associated with said grasper arm.

11. A tissue grasper assembly comprising:
    a capsule having a longitudinal axis;
    one or more resilient grasper arms expandable between a closed configuration extending along the longitudinal axis of said capsule, and an open configuration outside said capsule with said one or more grasper arms extending transversely away from the longitudinal axis of said capsule;
    a grasper surface, associated with at least one of said grasper arms, shaped and configured to engage a body tissue; and
    a controller coupling coupled to at least one of said grasper arms and movable to move said at least one grasper arm between the closed configuration and the open configuration;
    wherein:
    in the closed configuration of said one or more grasper arms, said one or more grasper arms present an atraumatic convex surface to body tissue; and
    in the open configuration of said one or more grasper arms, said grasper surface is directed proximally toward said capsule to engage body tissue.

12. The tissue grasper assembly of claim 11, further comprising a locking feature engageable to hold said tissue grasper assembly in a configuration engaging tissue.

13. The tissue grasper assembly of claim 11, wherein said capsule is configured for coupling with a distal end of a shaft.

14. The tissue grasper assembly of claim 11, wherein said capsule has a proximal end and a distal end, and one or more grasper arms extend from each of said proximal end and said distal end of said capsule.

15. The tissue grasper assembly of claim 11, further comprising a sharpened element extending distally from said tissue grasper assembly and configured for puncturing a body tissue wall.

16. The tissue grasper assembly of claim 11, wherein at least one of said grasper arms is resiliently held in an open configuration by a diverting feature formed on a distal end of said shaft.

17. The tissue grasper assembly of claim 11, wherein one or more of said grasper arms has a tissue grasping feature configured to engage tissue.

18. A method of manipulating tissue with a tissue-manipulating device, said method comprising:
    extending a tissue-manipulating device through a distal tissue wall to move a distal end of the tissue-manipulating device distal to the distal tissue wall, the tissue-manipulating device comprising a shaft with a longitudinal axis and a tissue grasper assembly, the tissue grasper assembly comprising at least one resiliently extendable grasper arm in a closed configuration extending along the shaft and with at least a portion of the at least one grasper arm within the shaft when the tissue-manipulating device, including a distal portion of the shaft, is extended through the distal tissue wall;
    actuating a tissue-manipulating device controller to extend the at least one resiliently extendable grasper arm from inside the shaft to outside the shaft to allow the at least one resiliently extendable grasper arm to expand into an open configuration extending transverse to the longitudinal axis of the shaft distal to the distal tissue wall; and
    moving the tissue-manipulating device proximally to engage the at least one grasper arm with the distal tissue wall and to move the distal tissue wall proximally.

19. The method of claim 18, further comprising:
    extending the tissue-manipulating device through a proximal tissue wall before extending the tissue-manipulating device through the distal tissue wall; and
    moving the tissue-manipulating device proximally to move the distal tissue wall in apposition to the proximal tissue wall.

20. The method of claim 19, further comprising separating the tissue grasper assembly from the shaft to deploy the tissue grasper assembly holding the proximal tissue wall and the distal tissue wall in apposition.

* * * * *